(12) United States Patent
Barta

(10) Patent No.: US 11,285,249 B2
(45) Date of Patent: Mar. 29, 2022

(54) DEVICES, SYSTEMS, AND METHODS FOR EVEN FLUID DISPERSION THROUGH HIGHER DENSITY MEDIA

(71) Applicant: Norman J. Barta, Fair Lawn, NJ (US)

(72) Inventor: Norman J. Barta, Fair Lawn, NJ (US)

( * ) Notice: Subject to any disclaimer, the term of this patent is extended or adjusted under 35 U.S.C. 154(b) by 0 days.

(21) Appl. No.: 16/802,348

(22) Filed: Feb. 26, 2020

(65) Prior Publication Data

US 2020/0268956 A1 Aug. 27, 2020

Related U.S. Application Data

(60) Provisional application No. 62/810,573, filed on Feb. 26, 2019.

(51) Int. Cl.
*A61M 1/16* (2006.01)

(52) U.S. Cl.
CPC ........ *A61M 1/1623* (2014.02); *A61M 1/1668* (2014.02); *A61M 1/1672* (2014.02); *A61M 2205/02* (2013.01); *A61M 2205/75* (2013.01)

(58) Field of Classification Search
CPC .............. A61M 1/1623; A61M 1/1668; A61M 1/1672; A61M 2205/02; A61M 2205/75; A61M 1/1696; B01J 2220/62
See application file for complete search history.

(56) References Cited

U.S. PATENT DOCUMENTS

| 9,707,330 B2 * | 7/2017 | Kelly | ................. | A61M 1/3609 |
| 2017/0189598 A1 * | 7/2017 | Slade | .................... | B01D 24/40 |

* cited by examiner

*Primary Examiner* — Krishnan S Menon
(74) *Attorney, Agent, or Firm* — Eric Kelly

(57) ABSTRACT

Various sorbent cartridges for use in sorbent dialysis are constructed to allow even dialysate stream flow through the sorbent cartridges, at relatively high flow rates, with sufficient engagement with sorbent media within the sorbent cartridges and without creating drill-through problems. The sorbent cartridges may have various columns and/or compartments for housing the sorbent media. The sorbent cartridges may have various horizontally oriented restrictors, with particularly sized holes, and with various vertically oriented side walls, that both form the various columns and/or compartments and that direct and control the dialysate stream through the sorbent cartridges in an even manner.

29 Claims, 12 Drawing Sheets

DEVICES, SYSTEMS, AND METHODS FOR EVEN FLUID DISPERSION THROUGH HIGHER DENSITY MEDIA

PRIORITY NOTICE

The present application claims priority under 35 U.S.C. § 119(e) to U.S. Provisional Patent Application Ser. No. 62/810,573 filed on Feb. 26, 2019, the disclosure of which is incorporated herein by reference in its entirety.

TECHNICAL FIELD OF THE INVENTION

The present invention relates in general to dialysate and more specifically to dialysate fluid mechanics and processing resulting in a more even dialysate fluid dispersion through higher density media.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Conventional hemodialysis therapy typically uses a reverse osmosis water system to process large volumes of essentially/typically tap water; wherein water usage can exceed 90 gallons in a typical four-hour hemodialysis treatment. The water processed by the reverse osmosis system is then combined with selected chemical elements to create a cleansing, salts-balanced fluid known as dialysate. Dialysate is then directed, in a counter-current fashion, through a filtering device, or dialyzer, where blood is flowing within the capillaries of the device and dialysate flows in the space surrounding the capillaries. Toxins and other undesirable elements are transferred to the dialysate via diffusion, or in some cases convection, across the membrane of the capillaries. The dialysate stream then carries these toxins to some form of drain.

An alternative approach, known as "sorbent dialysis," uses adsorbent materials (media), contained in a module, or cartridge, to remove toxins and other undesirable elements from the dialysate stream. Sorbent dialysis therefore recycles the dialysate, with no need for reverse osmosis water processing, reducing the water requirement to less than two gallons in a typical four-hour hemodialysis treatment.

Prior art sorbent cartridges have been commonly available for such sorbent based therapy for over 30 years. These prior art cartridges, in their earlier embodiments, tended to undesirably restrict the dialysate flow rate, such that treatments took too long. At low flow rates, e.g., in the area of 250 mL/min, the dialysate stream resided in the layers of the sorbent cartridge for sufficient duration to allow adsorption or conversion of the toxins and undesirable elements present within the dialysate stream. However, at higher and more desirable flow rates (where treatments would be more efficacious), an issue arose in these prior art sorbent cartridges where the dialysate stream created a condition known as "drill-through," whereby the dialysate stream would project through the adsorbent layers without full/proper fluid distribution within each layer, thus substantially reducing the adsorbent or other processing effect of the device. In other words, at higher flow rates with the prior art sorbent cartridges, the dialysate stream is not thoroughly or properly engaging with the sorbent media—many areas of the sorbent media, because of the drill-through, are not being utilized. Thus, high flow rates with the prior art sorbent cartridges resulted in poorly treated dialysate.

Prior art sorbent cartridges also consisted of a single containerized device. The adsorbent materials within the device are exhausted, or fully bound with toxins and other undesirable elements, at differing rates in the course of a hemodialysis treatment. The prior art sorbent cartridges therefore wasted capacity of certain elements, in that the entire cartridge was disposed of upon exhaustion of the least robust adsorbent material with respect to adsorbent capacity. That is, the prior art sorbent cartridges were largely single use and disposable, but were being disposed of after one use with some still-good media in them.

A need exists for an improved sorbent cartridge architecture that allows for higher dialysate flow rates, with even dispersion of the dialysate within the sorbent media cartridge layers that avoids or minimizes drill-through. The improved sorbent cartridges may also provide for separate modules, so that more robust sorbent elements can be cleansed and reused while exhausted sorbent elements are replaced more frequently.

It is to these ends that the present invention has been developed.

BRIEF SUMMARY OF THE INVENTION

To minimize the limitations in the prior art, and to minimize other limitations that will be apparent upon reading and understanding the present specification, the present invention describes various sorbent cartridges for use in sorbent dialysis. These sorbent cartridges may be configured to allow for even dialysate stream flow through the sorbent cartridges, at relatively high flow rates, with sufficient engagement with sorbent media within the sorbent cartridges and without creating drill-through problems. The sorbent cartridges may have various columns and/or compartments for housing the sorbent media. The sorbent cartridges may have various horizontally oriented restrictors, with particularly sized holes, and with various vertically oriented side walls, that both form the various columns and/or compartments and that direct and control the dialysate stream through the sorbent cartridges in an even manner.

In some embodiments, the sorbent cartridge may be rectangular in profile (the "rectangular cartridge"), with a square or rectangular footprint, to allow for easier shipping and storage in quantity. The casing/housing may be divided into (equally sized, in some embodiments) square or rectangular regions (columns and/or compartments) in a grid framework with respect to a transverse width cross-section. In some embodiments, the sorbent cartridge and most of its structural parts may be molded from various thermoplastics, such as, but not limited to, polycarbonate. In some embodiments, the sorbent cartridge may comprise a bottom cap, with a single (centered) entry port for the dialysate fluid to enter the bottom of the sorbent cartridge; a bottom chamber ending at a bottom restrictor, which regulates the fluid volume entering column(s)/compartments of that sorbent cartridge; the columnar construct formed by the sorbent cartridge grid (i.e., the columns and/or the compartments); then a top restrictor, which regulates the fluid volume leaving column(s)/compartment(s) of the sorbent cartridge; and a top cap, with a single (centered) exit port for fluid to exit the top of that sorbent cartridge.

In some embodiments, the sorbent cartridge may be substantially cylindrical on its outside, with a round or rounded footprint (the "round direct-flow cartridge"). In some embodiments, the cylindrical casing/housing may be divided into regions (compartments) using concentric cylindrical forms, with regions of various sizes depending on volume requirements for particular sorbent constituents/media that are placed within a region (compartment). In some embodiments, the concentric cylindrical forms may comprise a center cylindrical member, surrounded by one or more concentric cylindrical annular/ring members. In some embodiments, the sorbent cartridge and most of its structural parts may be molded from various thermoplastics, such as, but not limited to, polycarbonate. In some embodiments, the sorbent cartridge may comprise a bottom cap, with a single (centered) entry port for the dialysate fluid to enter the bottom of the sorbent cartridge; a bottom chamber ending in a bottom restrictor, which regulates the fluid volume entering compartment(s) of that sorbent cartridge; the compartment(s) (e.g., in concentric cylindrical format); a top restrictor, which regulates the fluid volume leaving the compartment(s) of that sorbent cartridge; and a top cap, with a single (centered) exit port for fluid to exit the top of that sorbent cartridge.

In some embodiments, the sorbent cartridge may be substantially cylindrical/conical on its outside, with an overall round or rounded footprint (the "segmented cartridge"). In some embodiments, the sorbent cartridge may comprise a substantially cylindrical casing/housing. In some embodiments, a main cylindrical section/region (e.g., between end-caps [e.g., between bottom cap and top cap]) may be divided into regions (e.g., compartments) using concentric cylindrical forms, with regions of various sizes depending on volume requirements for particular sorbent constituents that are placed within a region (compartment). In some embodiments, the concentric cylindrical forms may comprise a center cylindrical member, surrounded by one or more concentric cylindrical annular/ring members. In some embodiments, the sorbent cartridge and most of its structural parts may be molded from various thermoplastics, such as, but not limited to, polycarbonate. In some embodiments, the sorbent cartridge may comprise a bottom cap, with a single (centered) entry port for fluid to enter the bottom of the sorbent cartridge; a bottom chamber ending at a bottom restrictor, which regulates the fluid volume entering compartments of that sorbent cartridge; a series of compartments formed by concentric cylindrical forms; at least one interim restrictor(s) that may further moderate flow within the compartments; then a top restrictor, which regulates the fluid volume leaving compartment(s) of that sorbent cartridge; and a top cap, with a single (centered) exit port for fluid to exit the top of that sorbent cartridge.

In some embodiments, the sorbent cartridge may be substantially cylindrical on its outside, with a round or rounded footprint (a "reversing-flow cartridge"). In some embodiments, the sorbent cartridge may comprise a substantially cylindrical casing/housing. In some embodiments, a main cylindrical section/region (e.g., between end-caps [e.g., between bottom cap and top cap]) may be divided into regions (e.g., compartments) using concentric cylindrical forms, with regions of various sizes depending on volume requirements for particular sorbent constituents that are placed within a region (compartment). In some embodiments, the concentric cylindrical forms may comprise a center cylindrical member, surrounded by one or more concentric cylindrical annular/ring members. In some embodiments, the sorbent cartridge and most of its structural parts may be molded from various thermoplastics, such as, but not limited to, polycarbonate.

In some embodiments, cylindrical compartments may be formed from concentric vertical members. In some embodiments, some of the concentric vertical members may be attached to a bottom solid plate (e.g., a portion of the bottom cap); whereas, other of the concentric vertical members may be attached oppositely at a perforated surface, such that the concentric vertical members alternate with respect to where they are attached. In some embodiments, the concentric vertical members may be attached alternatively to bottom (e.g., the bottom solid plate) and top surfaces (e.g., the perforated surface), so that the tops of the first (innermost) and third dividers are open to the next-larger compartment, and the bottoms of the second and fourth dividers are open to the next-larger compartments. The fluid path reverses direction at these openings (gaps). In some embodiments, the sorbent cartridge may comprise a bottom cap, with a single (centered) entry port for fluid to enter the center column of the sorbent cartridge; concentric vertical members (cylindrical dividers), that divide the sorbent cartridge into regions (compartments) of various sizes; a perforated interim cap (e.g., the perforated surface), which is used in the manufacturing process to facilitate introduction of the sorbent materials (media) to the cylindrical regions (compartments); and a top cap, with a single (centered) exit port for fluid to exit the top of that sorbent cartridge.

In some embodiments, a system may comprise at least two cartridges, such as, but limited to, (a) any of the formerly described sorbent cartridges, combined with (b) a separable cartridge containing reusable material, such as, but not limited to, activated carbon. In some embodiments, the separable cartridge and its main structural parts may be molded from a thermoplastic, such as, but not limited to, polycarbonate. In some embodiments, the separable cartridge may comprise a bottom cap, with a single (centered) entry port for fluid to enter the bottom of the separable cartridge; an entry chamber, that allows the fluid to distribute across the bottom of the cartridge; a bottom restrictor, which regulates the fluid volume entering the cartridge; one or more compartments containing the reusable material (media); a top restrictor, which regulates the fluid volume leaving the cartridge; an exit chamber, that allows the fluid to pass out through the top restrictor prior to exiting the cartridge; and a top cap, with a single (centered) exit port for fluid to exit the top of the sorbent cartridge.

It is an objective of the present invention to provide sorbent cartridges for use in sorbent dialysis.

It is another objective of the present invention to provide sorbent cartridges for use in sorbent dialysis that may be used at relatively high flow rates (e.g., above 250 mL/min) without creating drill-through problems.

It is another objective of the present invention to provide sorbent cartridges for use in sorbent dialysis that may be used at relatively high flow rates (e.g., above 250 mL/min) while still exposing sufficient media within that sorbent cartridge for proper dialysate treatment.

It is another objective of the present invention to provide sorbent cartridges for use in sorbent dialysis, wherein such sorbent cartridges or portions thereof may be reused in more than one treatment.

It is another objective of the present invention to provide sorbent cartridges for use in sorbent dialysis, wherein such sorbent cartridges may be reused in more than one treatment, wherein spent/expired/exhausted media may be replaced as necessary.

It is another objective of the present invention to provide a system of sorbent cartridges that may be removably connected/attached in serial fashion.

It is yet another objective of the present invention to provide sorbent cartridges that may be configured to be readily portable/mobile by a single person without additional tools/devices.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 1A may contain five transverse-width sectional-lines, namely, sectional-line 1B-1B, sectional-line 1C-1C, sectional-line 1D-1D, sectional-line 1E-1E, and sectional-line 1F-1F.

FIG. 2A may contain three transverse-width sectional-lines, namely, sectional-line 2B-2B, sectional-line 2C-2C, and sectional-line 2D-2D.

FIG. 3A may contain five transverse-width sectional-lines, namely, sectional-line 3B-3B, sectional-line 3C-3C, sectional-line 3D-3D, sectional-line 3E-3E, and sectional-line 3F-3F.

FIG. 4A may contain three transverse-width sectional-lines, namely, sectional-line 4B-4B, sectional-line 4C-4C, and sectional-line 4D-4D.

FIG. 4F may contain two transverse-width sectional-lines, namely, sectional-line 4G-4G and sectional-line 4H-4H.

Figure 1A:
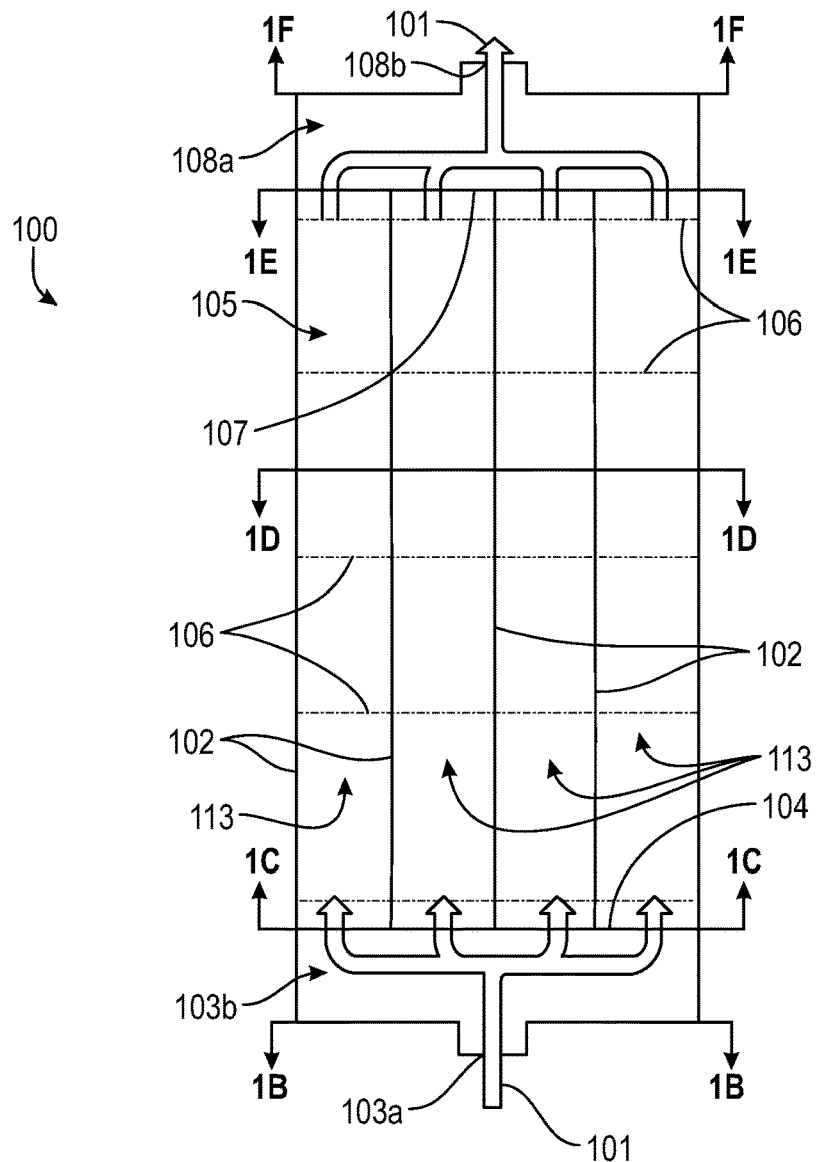
FIG. 1A may depict a schematic longitudinal cross-sectional diagram of a given sorbent cartridge.

REFERENCE NUMERAL SCHEDULE 100 sorbent cartridge 100
101 fluid path 101
102 vertical element 102
103a entry port 103a
103b bottom entry chamber 103b
104 bottom restrictor 104
105 compartment 105
106 layer 106
107 top restrictor 107
108a top exit chamber 108a
108b exit port 108b
111 hole 111
113 column 113
115 hole 115
200 sorbent cartridge 200
201 fluid path 201
202 vertical element 202
203b bottom entry chamber 203b
204 bottom restrictor 204
205 compartment 205
206 layer 206
207 top restrictor 207
208a top exit chamber 208a
211 hole 111
211a central set of holes 211a
211b inner annular/ring set of holes 211b
211c middle annular/ring set of holes 211c
211d outer most annular/ring set of holes 211d
215 hole 215
215a central set of holes 215a
215b inner annular/ring set of holes 215b
215c middle annular/ring set of holes 215c
215d outer most annular/ring set of holes 215d
300 sorbent cartridge 300
301 fluid path 301
305 compartment 305
307 restrictor 307
317 restrictor 317
321 holes 321
321a central set of holes 321a
321b inner annular/ring set of holes 321b
321c middle annular/ring set of holes 321c
321d outer most annular/ring set of holes 321d
325 holes 325
325a central set of holes 325a
325b inner annular/ring set of holes 325b
325c middle annular/ring set of holes 325c
325d outer most annular/ring set of holes 325d
400 sorbent cartridge 400
401 fluid path 401
401a fluid path 401a
401b fluid path 401b
401c fluid path 401c
401d fluid path 401d
401e fluid path 401e
401f fluid path 401f
401g fluid path 401g
402a alternating vertical concentric cylindrical elements 402a
402b alternating vertical concentric cylindrical elements 402b
403a perforated surface 403a
403b solid disk 403b
405a bottom restrictor 405a
405b semi-permeable membrane 405b
406 compartment 406
407 compartment 407
408 compartment 408
409 compartment 409
410 compartment 410
411 top chamber 411
412a top cap 412a
412b outermost cylinder 412b
415 hole 415
421 hole 421
425 semi-permeable membrane 425
441 bottom solid plate 441
501 fluid path 501
521 cartridge 521
531 first cartridge 531
533 second cartridge 533
535 third cartridge 535

DETAILED DESCRIPTION OF THE INVENTION

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be a cartridge configured for use in hemodialysis treatment, kidney dialysis, sorbent dialysis, combinations thereof, and/or the like.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be configured to receive a dialysate stream, treat that dialysate stream, and then expel that treated dialysate stream.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be comprise media for treating a dialysate stream. In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be comprise at least one compartment packed with media for treating a dialysate stream. In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be comprise a plurality of compartments, with at least one compartment, selected from the plurality of compartments, packed with media for treating a dialysate stream. In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may utilize different types of media.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be an elongate member that may be longer than it is wide. In some embodiments, at least one of the sorbent cartridges disclosed and discussed herein (e.g., sorbent cartridge 100, sorbent cartridge 521, first cartridge 531, second cartridge 533, third cartridge 535, combinations thereof, and/or the like) may be a rectilinear (rectangular prism) member (e.g., square or rectangle in cross-section) that may be longer than it is wide. In some embodiments, at least one of the sorbent cartridges disclosed and discussed herein (e.g., sorbent cartridge 200, sorbent cartridge 300, sorbent cartridge 400, sorbent cartridge 521, first cartridge 531, second cartridge 533, third cartridge 535, combinations thereof, and/or the like) may be a cylindrical member (e.g., circular or ovoid in cross-section) that may be longer than it is wide. In some embodiments, at least one of the sorbent cartridges disclosed and discussed herein (e.g., sorbent cartridge 300, sorbent cartridge 521, first cartridge 531, second cartridge 533, third cartridge 535, combinations thereof, and/or the like) may be a conical member (e.g., circular in cross-section and wider at one end than the other) that may be longer than it is wide.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may comprise an outer shell/housing, that may be solid and intended to be water tight.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may comprise at least one entry port (e.g., for a dialysate stream) and at least one exit port (e.g., for a treated dialysate stream). In some embodiments, the at least one entry port and the at least one exit port may be substantially oppositely disposed from each other.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be reusable, disposable, or partially reusable and then disposable.

In some embodiments, at least one of the sorbent cartridges disclosed and discussed herein (e.g., sorbent cartridge 100, sorbent cartridge 200, sorbent cartridge 300, sorbent cartridge 400, first cartridge 531, second cartridge 533, third cartridge 535, combinations thereof, and/or the like) may be configured for relatively high flow rates of a dialysate stream as compared against prior art, and without creating a drill-through problem.

In some embodiments, the sorbent cartridges disclosed and discussed herein (e.g., e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may be arranged in banks of at least two sorbent cartridges arranged in series, in parallel, combinations thereof, and/or the like.

In some embodiments, at least one of the sorbent cartridges disclosed and discussed herein (e.g., sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like) may also be characterized as a canister, module, a disk, container, vessel, combinations thereof, and/or the like.

Embodiments of sorbent cartridge 100 may be shown in figures FIG. 1A through and including FIG. 1F and discussed below.

Embodiments of sorbent cartridge 200 may be shown in figures FIG. 2A through and including FIG. 2D and discussed below.

Embodiments of sorbent cartridge 300 may be shown in figures FIG. 3A through and including FIG. 3F and discussed below.

Embodiments of sorbent cartridge 400 may be shown in figures FIG. 4A through and including FIG. 4H and discussed below.

Figure 5A:
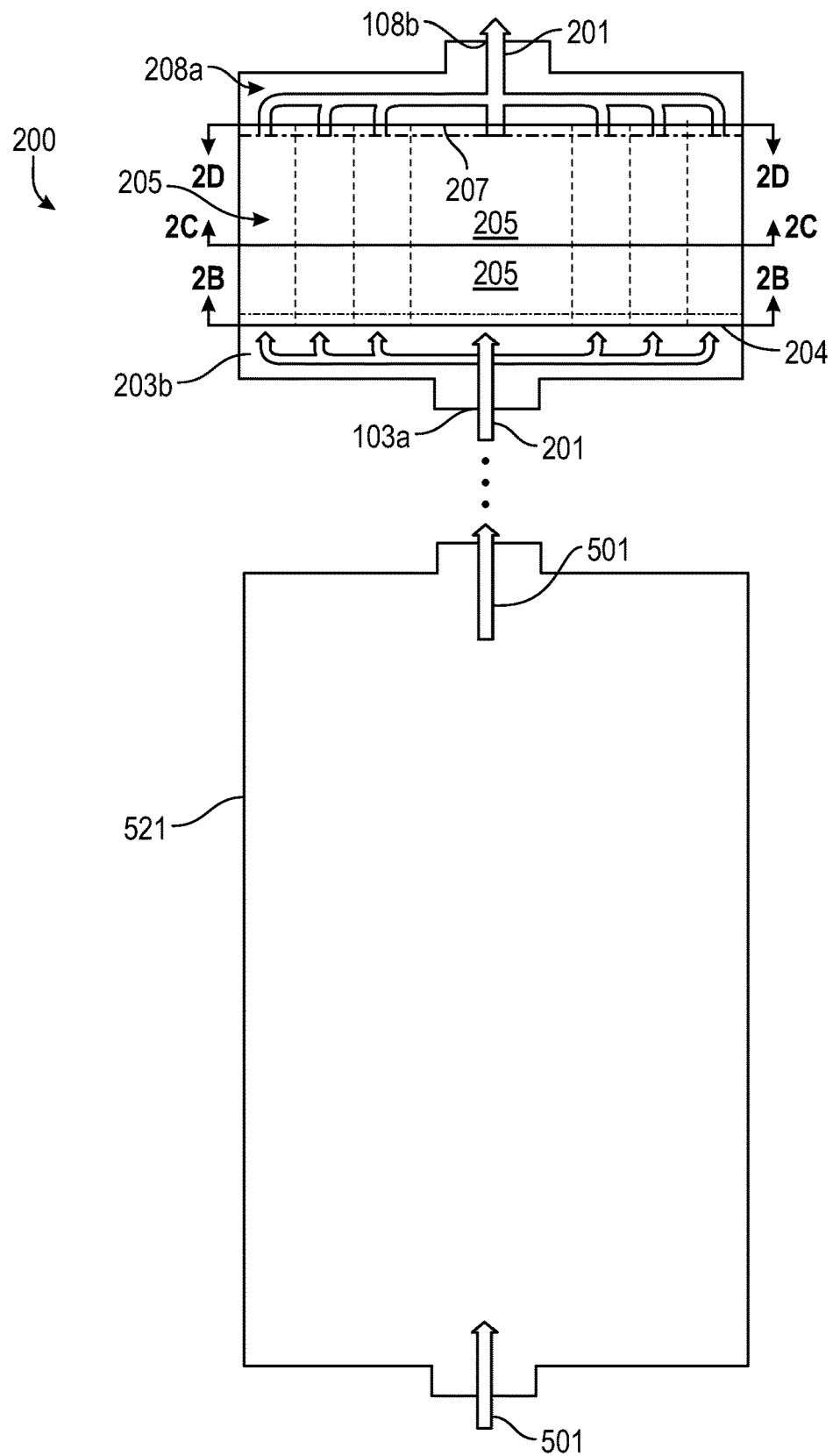
FIG. 5A may depict a schematic longitudinal cross-sectional diagram of a system of at least two cartridges arranged in series with respect to each other.

Embodiments of cartridge 521 may be shown in figure FIG. 5A.

Figure 5B:
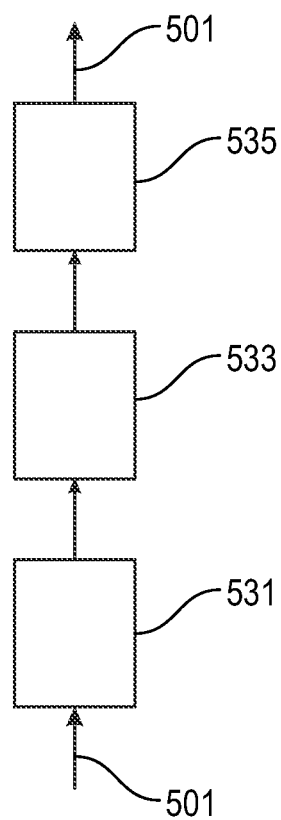
FIG. 5B may depict a schematic block diagram of a system of at least two sorbent cartridges arranged in series with respect to each other.

Embodiments of first cartridge 531, second cartridge 533, and/or third cartridge 535 may be shown in figure FIG. 5B.

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

Figure 1B:
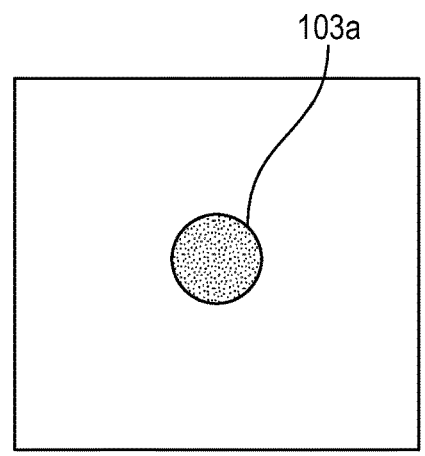
FIG. 1B may be a transverse-width cross-sectional diagram through sectional-line 1B-1B of FIG. 1A, showing a transverse-width cross-sectional portion of the sorbent cartridge of FIG. 1A.
Figure 1C:
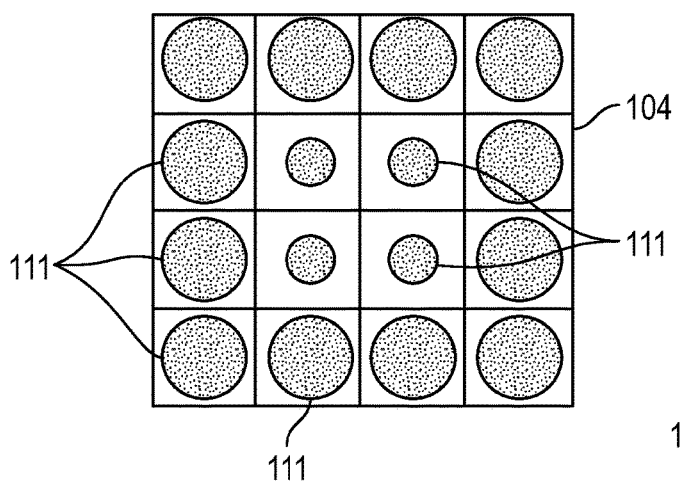
FIG. 1C may be a transverse-width cross-sectional diagram through sectional-line 1C-1C of FIG. 1A, showing a transverse-width cross-sectional portion of the sorbent cartridge of FIG. 1A.
Figure 1D:
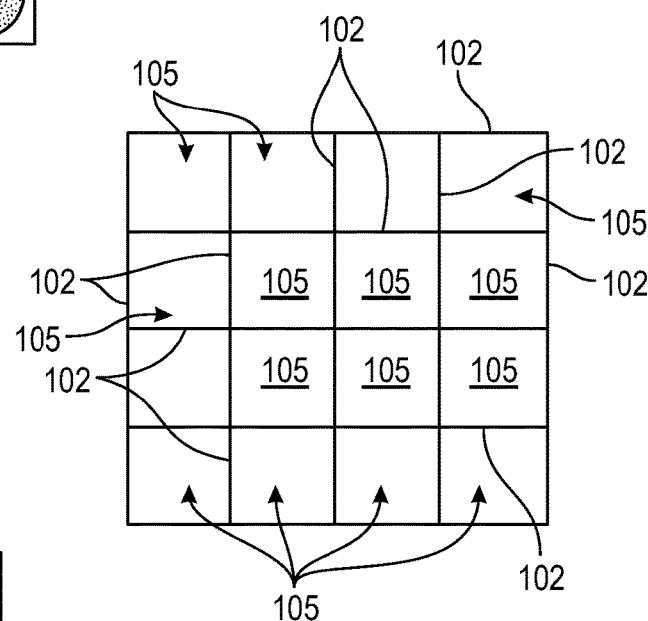
FIG. 1D may be a transverse-width cross-sectional diagram through sectional-line 1D-1D of FIG. 1A, showing a transverse-width cross-sectional portion of the sorbent cartridge of FIG. 1A.
Figure 1E:
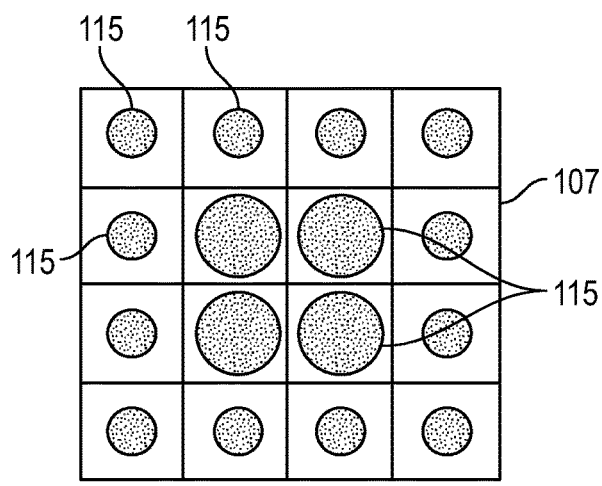
FIG. 1E may be a transverse-width cross-sectional diagram through sectional-line 1E-1E of FIG. 1A, showing a transverse-width cross-sectional portion of the sorbent cartridge of FIG. 1A.
Figure 1F:
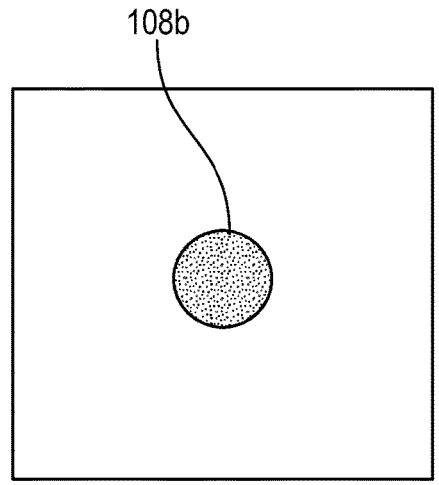
FIG. 1F may be a transverse-width cross-sectional diagram through sectional-line 1F-1F of FIG. 1A, showing a transverse-width cross-sectional portion of the sorbent cartridge of FIG. 1A.

FIG. 1A may depict a schematic longitudinal cross-sectional diagram of a sorbent cartridge 100. FIG. 1A may contain five transverse-width sectional-lines, namely, sectional-line 1B-1B (through an entry port 103*a*), sectional-line 1C-1C (through a bottom restrictor 104), sectional-line 1D-1D (through a middle region/portion of sorbent cartridge 100), sectional-line 1E-1E (through a top restrictor 107), and sectional-line 1F-1F (through an exit port 108*b*). FIG. 1B may be a transverse-width cross-sectional diagram through sectional-line 1B-1B of FIG. 1A, showing a transverse-width cross-sectional portion of sorbent cartridge 100 through entry port 103*a*. FIG. 1C may be a transverse-width cross-sectional diagram through sectional-line 1C-1C of FIG. 1A, showing a transverse-width cross-sectional portion of sorbent cartridge 100 through a bottom restrictor 104. FIG. 1D may be a transverse-width cross-sectional diagram through sectional-line 1D-1D of FIG. 1A, showing a transverse-width cross-sectional portion of the middle region of sorbent cartridge 100. FIG. 1E may be a transverse-width cross-sectional diagram through sectional-line 1E-1E of FIG. 1A, showing a transverse-width cross-sectional portion of sorbent cartridge 100 through the top restrictor 107. FIG. 1F may be a transverse-width cross-sectional diagram through sectional-line 1F-1F of FIG. 1A, showing a transverse-width cross-sectional portion of sorbent cartridge 100 through the exit port 108*b*. In some embodiments, sorbent cartridge 100 may be an example of the "rectangular cartridge."

In some embodiments, sorbent cartridge 100 may be a substantially rectilinear (rectangular prism) member (e.g., square or rectangle in cross-section) that may be longer than it is wide. In some embodiments, sorbent cartridge 100 may have a waterproof outer housing/shell, with at least one entry port 103a and at least one exit port 108b. In some embodiments, at least one entry port 103a and at least one exit port 108b may be substantially disposed opposite of each other on sorbent cartridge 100. In some embodiments, flow path 101 may be a flow path of a dialysate stream through sorbent cartridge 100 shown in FIG. 1A. In some embodiments, fluid (e.g., the dialysate stream) may enter sorbent cartridge 100 through at least one entry port 103a. In some embodiments, treated fluid may exit sorbent cartridge 100 through at least one exit port 108b. In some embodiments, at least one entry port 103a and/or at least one exit port 108b may be outfitted with valves, check-valves, hose barbs, luer-locks, threads, combinations thereof, and/or the like. The entry port 103a may have, as part of its construct, a unique connection arrangement to allow that sorbent cartridge 100 to be joined (removably so in some embodiments) in a water-tight fashion to the underlying systems for which it is designed. See e.g., FIG. 1A, FIG. 1B, and FIG. 1F.

In some embodiments, at least one entry port 103a may be attached to a bottom entry chamber 103b of sorbent cartridge 100. In some embodiments, bottom entry chamber 103b may be a holding chamber of a predetermined and fixed volume for the fluid (used before the fluid enters column(s) 113/compartment(s) 105). See e.g., FIG. 1A. After the fluid enters at least one entry port 103a, the fluid may be in bottom entry chamber 103b. In some embodiments, the fluid may exit bottom entry chamber 103b through bottom restrictor 104. See e.g., FIG. 1A and FIG. 1C. In some embodiments, bottom restrictor 104 may be a solid plate with a plurality of through holes 111. See e.g., FIG. 1C.

In some embodiments, each such through hole 111 (of bottom restrictor 104) may lead to a column 113. In some embodiments, each such through hole 111 may be in communication with a given column 113. In some embodiments, sorbent cartridge 100 may comprise a plurality of columns 113. In some embodiments, a given column 113, selected from the plurality of columns 113, may be bound at its bottom by a portion of bottom restrictor 104 and at its top by a portion of a top restrictor 107. In some embodiments, a given column 113, selected from the plurality of columns 113, may be a rectangular prism member, that may be longer than wide, and longer than deep. See e.g., FIG. 1A and FIG. 1D. In some embodiments, a given column 113 may be separated from other columns 113 by one or more vertical element(s) 102. In some embodiments, a given column 113 may comprise at least one compartment 105. In embodiments where a given column 113 may comprise two or more compartments 105, those compartments may be stacked vertically, end-to-end, in a serial fashion, with each such compartment 105 separated by a layer 106. In some embodiments, media of a given compartment 105 may be separated by a semi-permeable membrane, designated layer 106, so as to keep the media of one given compartment 106 from shifting and/or mixing into a vertically adjacent compartment 105. For example, and without limiting the scope of the current invention, FIG. 1A may show four columns 113, wherein each such column 113 may comprise four compartments 105 (vertically stacked end-to-end), and thus three layers 106 per column 113; whereas, the cross-section through the middle portion/region of sorbent cartridge shown in FIG. 1D may show sixteen columns 113. In some embodiments, each through hole 111 may lead to a compartment 105 (of a given column 113). In some embodiments, each compartment 105 may be vertically bounded by one or more vertical element(s) 102. In some embodiments, each column 113 may be substantially packed with the media. In some embodiments, each compartment 105 may be substantially packed with the media. In some embodiments, at least one column 113 may be substantially packed with the media. In some embodiments, at least one compartment 105 may be substantially packed with the media. In some embodiments, at least one compartment 105 of sorbent cartridge 100 may comprise the media. In some embodiments, the media may comprise various predetermined sorbent materials, in an order and of a quantity to achieve the toxin adsorption and conversion required/desired. In some embodiments, a given layer 106 may permit the fluid (e.g., the dialysate stream) to readily pass through that given layer 106; but that given layer 106 may substantially block/prevent passage of the media. In some embodiments, a given vertical element 102 may block/prevent both the fluid (e.g., the dialysate stream) and the media from passing through that given vertical element 102. See e.g., FIG. 1A, FIG. 1C, FIG. 1D, and FIG. 1E.

In some embodiments, top restrictor 107 may be a solid plate with a plurality of through holes 115. See e.g., FIG. 1E. In some embodiments, each column 113 may end/terminate at a portion of top restrictor 107. In some embodiments, each column 113 may be in communication with a hole 115 selected from the plurality of holes 115. In some embodiments, each column 113 may lead to a hole 115 selected from the plurality of holes 115. Thus, the fluid may enter a given column 113 through a given hole 111 and that fluid may leave that column 113 through a given hole 115. Before that fluid leaves that column 113, that fluid may interact with the media that may reside within that column 113 and the compartment(s) 105 that may make up that given column 113. In some embodiments, each such through hole 111 may lead to a compartment 105 (of a given column 113). In some embodiments, each compartment 105 may be vertically bounded by one or more vertical element(s) 102. See e.g., FIG. 1A, FIG. 1D, and FIG. 1E.

The fluid path 101 may be obstructed (or partially obstructed) by bottom restrictor 104 that directs the fluid into each column 113 (beginning with a first compartment 105 for that given column 113). The bottom restrictor 104 contains openings (holes 111) of varied (but fixed) sizes to more evenly distribute the fluid across the columns 113/compartments 105. See e.g., FIG. 1C.

In some embodiments, the plurality of holes 111 of bottom restrictor 104 may be of fixed (non-variable) and predetermined size(s). In some embodiments, the plurality of holes 111 of bottom restrictor 104 may be different sizes (e.g., diameters). In some embodiments, holes 111 closer to an outside edge/exterior of bottom restrictor 104 may be larger than holes 111 located closer to a center of bottom restrictor 104. Because Newtonian fluids often seek a path of least resistance, this difference in hole 111 size may encourage the fluid to utilize both centrally located holes 111 and holes 111 located closer to the outside edge/exterior of bottom restrictor 104. See e.g., FIG. 1C.

In some embodiments, the plurality of holes 115 of top restrictor 107 may be of fixed (non-variable) and predetermined size(s). In some embodiments, the plurality of holes 115 of top restrictor 107 may be different sizes (e.g., diameters). In some embodiments, holes 115 closer to an outside edge/exterior of top restrictor 107 may be smaller than holes 115 located closer to a center of top restrictor 107. See e.g., FIG. 1E.

In some embodiments, for a given column 113, a size (e.g., a diameter) of the hole 111 the leads into that column 113 may be of a different size with respect to the hole 115 that provides an exit for that column 113. Compare FIG. 1C to FIG. 1E.

In some embodiments, for holes 111 that may be larger, that may be located closer to the outside exterior of bottom restrictor 104, those corresponding columns 113 may then lead to holes 115 that may be smaller than the holes 111 leading into those columns 113. Whereas in contrast, in some embodiments, for holes 111 that may be smaller, that may be located closer to the center of bottom restrictor 104, those corresponding columns 113 may then lead to holes 115 that may be larger than the holes 111 leading into those columns 113. See e.g., FIG. 1A, FIG. 1C, and FIG. 1E.

In some embodiments, top restrictor 107 may lead to a top exit chamber 108a of that sorbent cartridge 100. In some embodiments, the plurality of holes 115 (of top restrictor 107) may lead to top exit chamber 108a. In some embodiments, the plurality of holes 115 (of top restrictor 107) may be in communication with top exit chamber 108a. In some embodiments, each column 113 may empty out into top exit chamber 108a. In some embodiments, top exit chamber 108a may be a holding chamber of a predetermined and fixed volume for the fluid (used before the fluid finally exits that sorbent cartridge 100 through exit port 108b). See e.g., FIG. 1A and FIG. 1F. In some embodiments, top exit chamber 108a may be disposed opposite from bottom entry chamber 103b, with columns 113 disposed between top exit chamber 108a and bottom entry chamber 103b. See e.g., FIG. 1A.

When the fluid has passed through the sorbent materials (the media) of the columns 113 (and its compartments 105), the fluid achieves the top restrictor 107. The top restrictor 107 may comprise openings (e.g., holes 115) of varied, but fixed, sizes to moderate evenly the flow of fluid exiting the columns 113. The fluid then enters top exit chamber 108a, which allows the fluid to pass out through the top restrictor 107 prior to exiting that sorbent cartridge 100. The fluid then exits through exit port 108b, designed to accommodate tubing/piping/plumbing as required/desired.

Note, while FIG. 1A may show sorbent cartridge 100 located with entry port 103a located vertically at a bottom and exit port 108b located vertically at a top; sorbent cartridge 100 may also be operated in a horizontal fashion, a diagonal fashion, or with entry port 103a located vertically at the top and exit port 108b located vertically at the bottom (i.e., in a configuration that is opposite to what is shown in FIG. 1A).

Figure 2A:
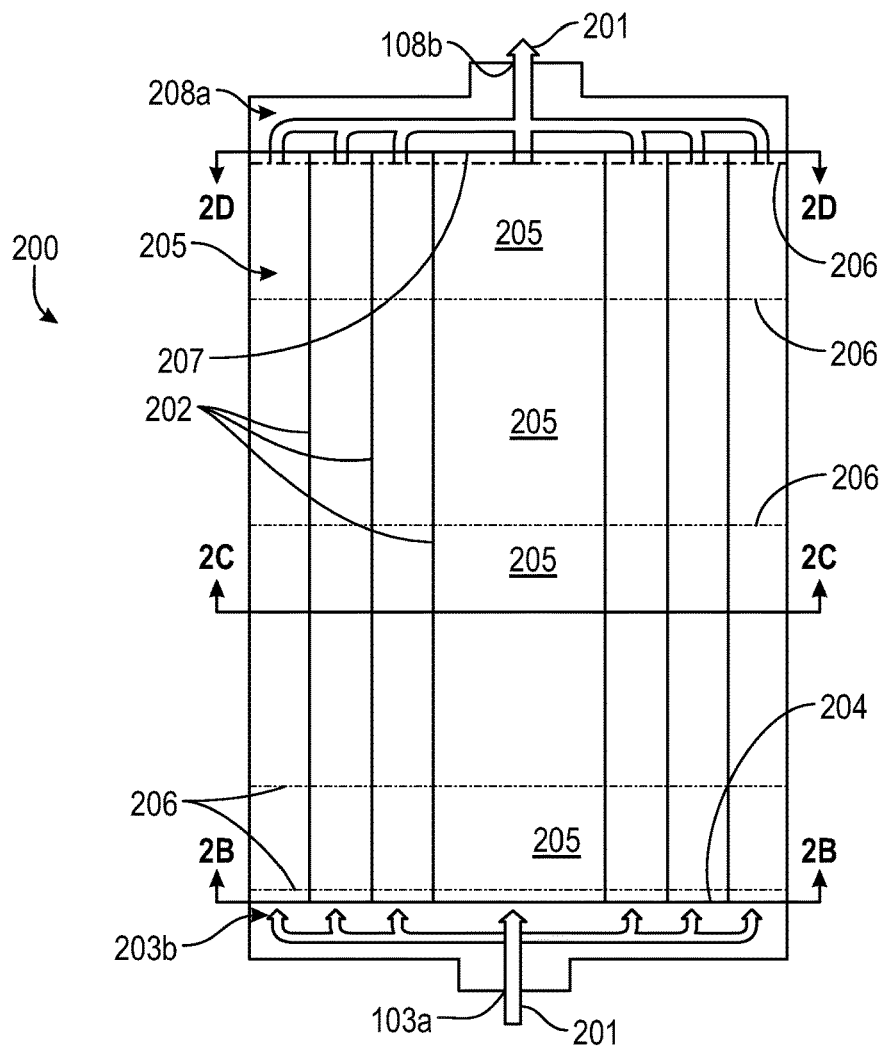
FIG. 2A may depict a schematic longitudinal cross-sectional diagram of a given sorbent cartridge.
Figure 2B:
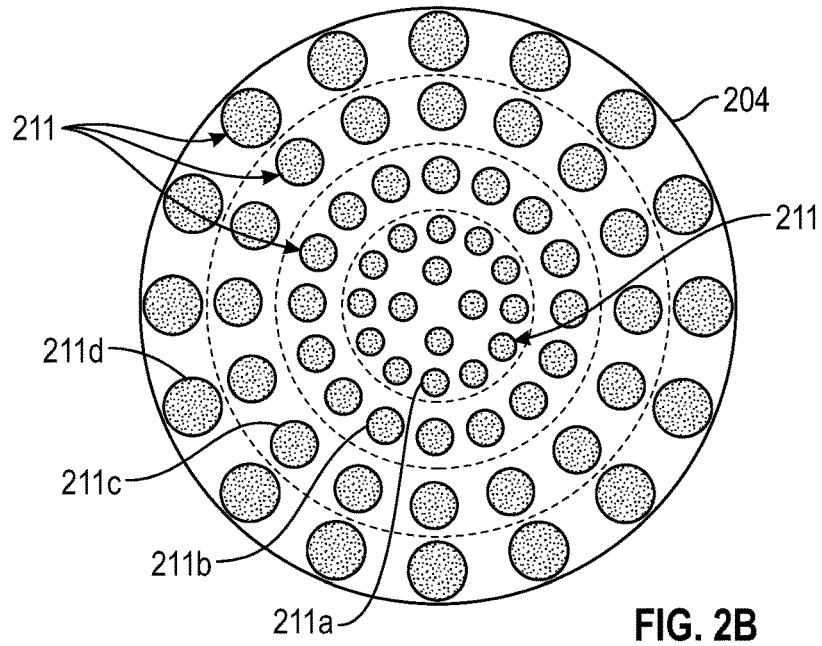
FIG. 2B may be a transverse-width cross-sectional diagram through sectional-line 2B-2B of FIG. 2A, showing a transverse-width cross-sectional portion of the sorbent cartridge of FIG. 2A.
Figure 2C:
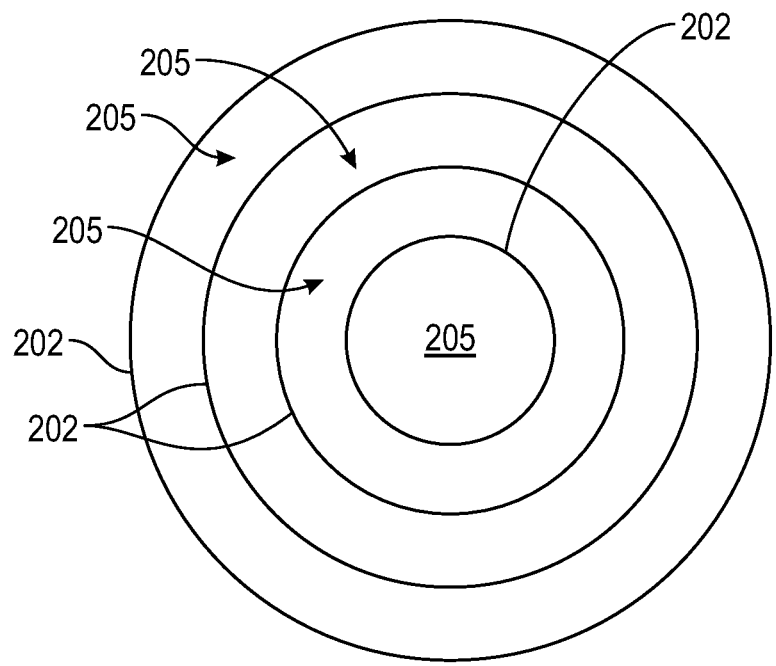
FIG. 2C may be a transverse-width cross-sectional diagram through sectional-line 2C-2C of FIG. 2A, showing a transverse-width cross-sectional portion of the sorbent cartridge of FIG. 2A.
Figure 2D:
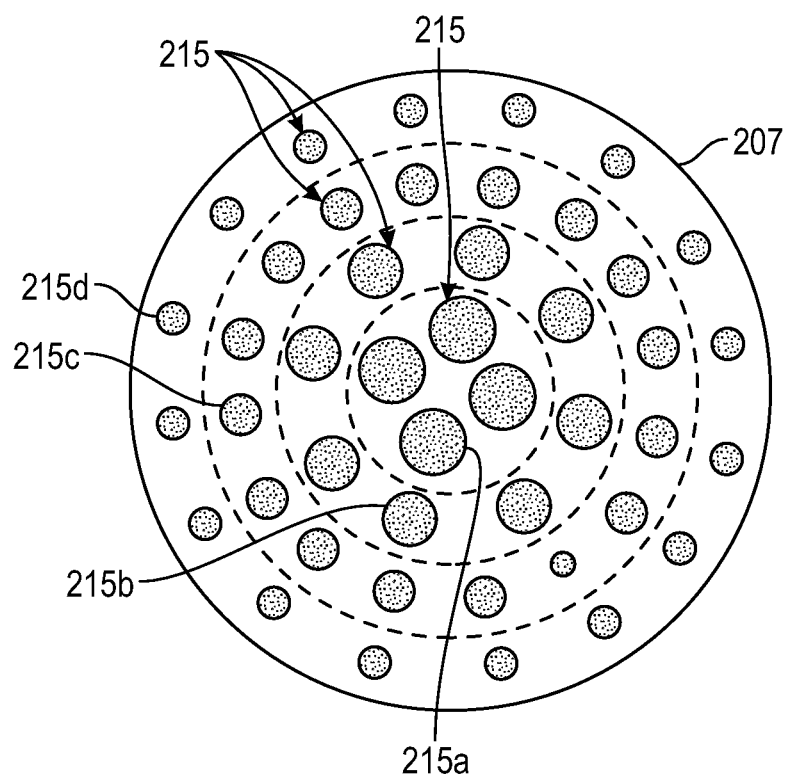
FIG. 2D may be a transverse-width cross-sectional diagram through sectional-line 2D-2D of FIG. 2A, showing a transverse-width cross-sectional portion of the sorbent cartridge of FIG. 2A.

FIG. 2A may depict a schematic longitudinal cross-sectional diagram of a sorbent cartridge 200. FIG. 2A may contain three transverse-width sectional-lines, namely, sectional-line 2B-2B (through a bottom restrictor 204), sectional-line 2C-2C (through a middle region/portion of sorbent cartridge 200), and sectional-line 2D-2D (through a top restrictor 207). FIG. 2B may be a transverse-width cross-sectional diagram through sectional-line 2B-2B of FIG. 2A, showing a transverse-width cross-sectional portion of sorbent cartridge 200 through bottom restrictor 204. FIG. 2C may be a transverse-width cross-sectional diagram through sectional-line 2C-2C of FIG. 2A, showing a transverse-width cross-sectional through the middle region/portion of sorbent cartridge 200. FIG. 2D may be a transverse-width cross-sectional diagram through sectional-line 2D-2D of FIG. 2A, showing a transverse-width cross-sectional portion of sorbent cartridge 200 through top restrictor 207. In some embodiments, sorbent cartridge 200 may be an example of the "round direct-flow cartridge."

In some embodiments, sorbent cartridge 200 may be substantially similar to sorbent cartridge 100 in terms of function and purpose; however, sorbent cartridge 200 and sorbent cartridge 100 may differ structurally in some respects. Where sorbent cartridge 100 may utilize a plurality of rectangular prism columns 113 (each with at least one compartment 105); sorbent cartridge 200 may utilize concentric cylindrical ring/annular compartments 205 and a central cylindrical compartment 205, each of which may be vertically bounded by vertical elements 202; otherwise, sorbent cartridge 200 and sorbent cartridge 100 may be substantially similar structurally. For example and without limiting the scope of the present invention: sorbent cartridge 100 entry port 103a may be substantially similar to identical structurally with sorbent cartridge 200 entry port 103a; sorbent cartridge 100 exit port 108b may be substantially similar to identical structurally with sorbent cartridge 200 exit port 108b; sorbent cartridge 100 may have substantially similar to identical materials of construction as sorbent cartridge 200; sorbent cartridge 100 and sorbent cartridge 200 may be both elongate members; sorbent cartridge 100 may have vertical elements 102 that may form the vertical structures of the columns 113 and compartments 105, whereas, sorbent cartridge 200 may have vertical elements 202 that may form the vertical structures of compartments 205; sorbent cartridge 100 may have bottom entry chamber 103b while sorbent cartridge 200 may have a bottom entry chamber 203b, wherein both bottom entry chambers may serve same functions, but be of different shapes; sorbent cartridge 100 may have top exit chamber 108a while sorbent cartridge 200 may have a top exit chamber 208a, wherein both top entry chambers may serve same functions, but be of different shapes; sorbent cartridge 100 may have bottom restrictor 104 while sorbent cartridge 200 may have a bottom restrictor 204, wherein both bottom restrictors may serve same functions, but be of different shapes; sorbent cartridge 100 may have top restrictor 107 while sorbent cartridge 200 may have a top restrictor 207, wherein both top restrictors may serve same functions, but be of different shapes; and sorbent cartridge 100 may have layer(s) 106 while sorbent cartridge 200 may have layer(s) 206, wherein both types of layers may serve same function and be made of a same material(s), but be of different shapes.

In some embodiments, sorbent cartridge 200 may be a substantially cylindrical member (e.g., circular or elliptical in cross-section) that may be longer than is wide. In some embodiments, sorbent cartridge 200 may have a waterproof outer housing/shell, with at least one entry port 103a and at least one exit port 108b. In some embodiments, at least one entry port 103a and at least one exit port 108b may be substantially disposed opposite of each other on sorbent cartridge 200. In some embodiments, flow path 201 may be a flow path of a dialysate stream through sorbent cartridge 200 shown in FIG. 2A. In some embodiments, fluid (e.g., the dialysate stream) may enter sorbent cartridge 200 through at least one entry port 103a. In some embodiments, treated fluid may exit sorbent cartridge 200 through at least one exit port 108b. In some embodiments, at least one entry port 103a and/or at least one exit port 108b may be outfitted with valves, check-valves, hose barbs, luer-locks, threads, combinations thereof, and/or the like. The entry port 103a may have, as part of its construct, a unique connection arrangement to allow that sorbent cartridge 200 to be joined (removably so in some embodiments) in a water-tight fashion to the underlying systems for which it is designed. See e.g., FIG. 2A.

In some embodiments, at least one entry port 103a may be attached to a bottom entry chamber 203b of sorbent cartridge 200. In some embodiments, bottom entry chamber 203b may be a holding chamber of a predetermined and fixed volume for the fluid (used before the fluid enters compartment(s) 205). See e.g., FIG. 2A. After the fluid enters at least one entry port 103a, the fluid may be in bottom entry chamber 203b. In some embodiments, the fluid may exit bottom entry chamber 203b through bottom restrictor 204. See e.g., FIG. 2A and FIG. 2B. In some embodiments, bottom restrictor 204 may be a solid plate with a plurality of through holes 211. See e.g., FIG. 2B.

In some embodiments, each such through hole 211 (of bottom restrictor 204) may lead to a compartment 205. In some embodiments, each such through hole 211 may be in communication with a given compartment 205. In some embodiments, sorbent cartridge 200 may comprise a plurality of compartments 205. In some embodiments, a given compartment 205, selected from the plurality of compartments 205, may be bound at its bottom by a portion of bottom restrictor 204 and at its top by a portion of a top restrictor 207. In some embodiments, a given compartment 205, selected from the plurality of compartments 205, may be a concentric cylindrical ring/annular member or cylindrical member for a center compartment 205, that may be longer than wide. See e.g., FIG. 2A and FIG. 2C. In some embodiments, a given compartment 205 may be separated from other compartments 205 by one or more vertical element(s) 202. In some embodiments, with respect to a vertical direction in FIG. 2A, a lower post compartment 205 (e.g., in communication with bottom restrictor 204) may have one or more additional compartments 205 stacked, end-on-end, above that lowest compartment 205. For the annular/ring like cylindrical compartments 205, that may be similar to a stack of rings or a stack of donuts. For the central compartments 205 that may be a cylinder, this may similar to a stack of disks or a stack of coins. In some embodiments, between each vertically stacked adjacent compartments may be a layer 206. In some embodiments, media of a given compartment 205 may be separated by a semi-permeable membrane, designated layer 206, so as to keep the media of one given compartment 206 from shifting and/or mixing into a vertically adjacent compartment 205. For example, and without limiting the scope of the current invention, FIG. 2C may show four compartments 205, (one central cylindrical compartment 205 and three concentric cylindrical ring/annular compartments 205 disposed around that one central cylindrical compartment 205). For example, and without limiting the scope of the current invention, FIG. 2C may show sixteen compartments 205 (four vertically stacked cylindrical compartments 205; four inner most cylindrical annular/ring compartments 205 disposed around the four vertically stacked cylindrical compartments 205; four middle cylindrical annular/ring compartments 205 disposed around the four inner most cylindrical annular/ring compartments 205; and four outer most cylindrical annular/ring compartments 205 disposed around the four middle cylindrical annular/ring compartments 205). In some embodiments, each through hole 211 may lead to a lower most compartment 205. In some embodiments, each compartment 205 may be vertically bounded by one or more vertical element(s) 202. In some embodiments, each compartment 205 may be substantially packed with the media. In some embodiments, at least one compartment 205 may be substantially packed with the media. In some embodiments, at least one compartment 205 of sorbent cartridge 200 may comprise the media. In some embodiments, the media may comprise various predetermined sorbent materials, in an order and of a quantity to achieve the toxin adsorption and conversion required/desired. In some embodiments, a given layer 206 may permit the fluid (e.g., the dialysate stream) to readily pass through that given layer 206; but that given layer 206 may substantially block/prevent passage of the media. In some embodiments, a given vertical element 202 may block/prevent both the fluid (e.g., the dialysate stream) and the media from passing through that given vertical element 202. See e.g., FIG. 2A, FIG. 2B, FIG. 2C, and FIG. 2D.

In some embodiments, top restrictor 207 may be a solid plate with a plurality of through holes 215. See e.g., FIG. 2D. In some embodiments, each top most compartment 205 may end/terminate at a portion of top restrictor 207. In some embodiments, each top most compartment 205 may be in communication with at least one hole 215 selected from the plurality of holes 215. In some embodiments, each top most compartment 205 may lead to at least one hole 215 selected from the plurality of holes 215. Thus, the fluid may enter a given lower most compartment 205 through a given hole 211 and that fluid may leave a top most compartment 205, that may be linearly and vertically located above that same given lower most compartment 205, through a given hole 215. Before that fluid leaves that same linearly and vertically stack of compartments 205, that fluid may interact with the media that may reside within at least one of those compartments 205. In some embodiments, each such through hole 211 may lead to a lower most compartment 205. In some embodiments, each compartment 205 may be vertically bounded by one or more vertical element(s) 202. See e.g., FIG. 2A, FIG. 2B, and FIG. 2D.

The fluid path 201 may be obstructed (or partially obstructed) by bottom restrictor 204 that directs the fluid into each lower most compartment 205. The bottom restrictor 204 contains openings (holes 211) of varied (but fixed) sizes to more evenly distribute the fluid across the compartments 205. See e.g., FIG. 2A and FIG. 2B.

In some embodiments, the plurality of holes 211 of bottom restrictor 204 may be of fixed (non-variable) and predetermined size(s). In some embodiments, the plurality of holes 211 of bottom restrictor 204 may be different sizes (e.g., diameters). In some embodiments, holes 211 closer to an outside edge/exterior of bottom restrictor 204 may be larger than holes 211 located closer to a center of bottom restrictor 204. In some embodiments, the plurality of holes 211 may be arranged into distinct sets of holes 211 corresponding to specific lower most compartments 205. In some embodiments, for each different lower most compartment 205 there may be a distinct set of holes 211 serving just that specific lower most compartment 205. In some embodiments, for each different lower most compartment 205 there may be a distinct set of holes 211 that lead to just that specific lower most compartment 205. In some embodiments, for each different lower most compartment 205 there may be a distinct set of holes 211 that are in communication with just that specific lower most compartment 205. For example, and without limiting the scope of the present invention, as shown in FIG. 2A there may be four lower most compartments 205: a centrally located lower most compartment 205; an inner most and lowest cylindrical annular/ring compartment 205 disposed concentrically around the centrally located lower most compartment 205; a middle and lowest cylindrical annular/ring compartment 205 disposed concentrically around the inner most and lowest cylindrical annular/ring compartment 205; and an outer most and lowest cylindrical annular/ring compartment 205 disposed concentrically around the middle and lowest cylindrical annular/ring compartment 205. Each of these four lower most compartments 205 may be in communication with a different set of holes 211 from a distinct region of bottom restrictor 204. For example, and without limiting the scope of the present invention, bottom restrictor 204 may have: a central region of a first set of holes 211a of a particular size (e.g., a first size) wherein these first set of holes 211a are in communication with the centrally located lower most compartment 205; an inner most annular/ring region of a second set of holes 211b of a particular size (e.g., a second size), wherein these second set of holes 211b are in communication with the inner most and lowest cylindrical annular/ring compartment 205; a middle annular/ring region of a third set of holes 211c of a particular size (e.g., a third size), wherein these third set of holes 211c are in communication with the middle and lowest cylindrical annular/ring compartment 205; and an outer most annular/ring region of a fourth set of holes 211d of a particular size (e.g., a fourth size), wherein these fourth set of holes 211d are in communication with the outer most and lowest cylindrical annular/ring compartment 205. In some embodiments, the first size, the second size, the third size, and the fourth size of the holes 211 may each be a different size (e.g., diameter) with respect to each other. In some embodiments, the first size may be smaller than the second size, the second size may be smaller than the third size, and the third size may be smaller than the fourth size. In some embodiments, the first size (for central set of holes 211a) may be the smallest size of the holes 211 of bottom restrictor 204. In some embodiments, the fourth size (for outer most annular/ring set of holes 211d) may be the largest size of the holes 211 of bottom restrictor 204. Because Newtonian fluids often seek a path of least resistance, this difference in hole 211 size, from the center to the outside, may encourage the fluid to utilize both centrally located holes 211 and holes 211 located closer to the outside edge/exterior of bottom restrictor 204. See e.g., FIG. 2A and FIG. 2B.

In some embodiments, the plurality of holes 215 of top restrictor 207 may be of fixed (non-variable) and predetermined size(s). In some embodiments, the plurality of holes 215 of top restrictor 207 may be different sizes (e.g., diameters). In some embodiments, holes 215 closer to an outside edge/exterior of top restrictor 207 may be smaller than holes 215 located closer to a center of top restrictor 207. In some embodiments, the plurality of holes 215 may be arranged into distinct sets of holes 215 corresponding to specific top most compartments 205. In some embodiments, for each different top most compartment 205 there may be a distinct set of holes 215 serving just that specific top most compartment 205. In some embodiments, for each different top most compartment 205 there may be a distinct set of holes 215 that lead to just that specific top most compartment 205. In some embodiments, for each different top most compartment 205 there may be a distinct set of holes 215 that are in communication with just that specific top most compartment 205. For example, and without limiting the scope of the present invention, as shown in FIG. 2A there may be four top most compartments 205: a centrally located top most compartment 205; an inner most and highest cylindrical annular/ring compartment 205 disposed concentrically around the centrally located top most compartment 205; a middle and highest cylindrical annular/ring compartment 205 disposed concentrically around the inner most and highest cylindrical annular/ring compartment 205; and an outer most and highest cylindrical annular/ring compartment 205 disposed concentrically around the middle and highest cylindrical annular/ring compartment 205. Each of these four top most compartments 205 may be in communication with a different set of holes 215 from a distinct region of top restrictor 207. For example, and without limiting the scope of the present invention, top restrictor 207 may have: a central region of a first set of holes 215a of a particular size (e.g., a first size) wherein these first set of holes 215a are in communication with the centrally located top most compartment 205; an inner most annular/ring region of a second set of holes 215b of a particular size (e.g., a second size), wherein these second set of holes 215b are in communication with the inner most and highest cylindrical annular/ring compartment 205; a middle annular/ring region of a third set of holes 215c of a particular size (e.g., a third size), wherein these third set of holes 215c are in communication with the middle and highest cylindrical annular/ring compartment 205; and an outer most annular/ring region of a fourth set of holes 215d of a particular size (e.g., a fourth size), wherein these fourth set of holes 215d are in communication with the outer most and highest cylindrical annular/ring compartment 205. In some embodiments, the first size, the second size, the third size, and the fourth size of the holes 215 may each be a different size (e.g., diameter) with respect to each other. In some embodiments, the first size may be larger than the second size, the second size may be larger than the third size, and the third size may be larger than the fourth size. In some embodiments, the first size (for central set of holes 215a) may be the largest size of the holes 215 of top restrictor 207. In some embodiments, the fourth size (for outer most annular/ring set of holes 215d) may be the smallest size of the holes 215 of top restrictor 207. See e.g., FIG. 2A and FIG. 2D.

In some embodiments, for a given stack of vertically arranged compartments 205, a size (e.g., a diameter) of the hole 211 the leads into the lower most compartment 205 of that given stack of vertically arranged compartments 205 may be of a different size with respect to the hole 215 that provides an exit for the top most compartment 205 of that given stack of vertically arranged compartments 205. Compare FIG. 2B to FIG. 2D.

In some embodiments, for holes 211 that may be larger, that may be located closer to the outside exterior of bottom restrictor 204, those corresponding compartments 205 of that given stack of vertically arranged compartments 205 may then lead to holes 215 that may be smaller than the corresponding holes 211 leading into the lower most compartment 205 of that given stack of vertically arranged compartments 205. Whereas in contrast, in some embodiments, for holes 211 that may be smaller, that may be located closer to the center of bottom restrictor 204, those corresponding compartments 205 of that given stack of vertically arranged compartments 205 may then lead to holes 215 that may be larger than the holes 211 leading into the lower most compartment 205 of that given stack of vertically arranged compartments 205. See e.g., FIG. 2A, FIG. 2B, and FIG. 2D.

In some embodiments, central set of holes 211a may be in direct linear (colinear) and vertical alignment with central set of holes 215a (with a directly shared portion of fluid path 201), with centrally located compartment(s) 205 disposed between central set of holes 211a and central set of holes 215a, wherein fluid entering central set of holes 211a will exit central set of holes 215a. In some embodiments, the hole sizes of central set of holes 211a may differ from the hole sizes of central set of holes 215a. In some embodiments, a quantity of central set of holes 211a may differ from a quantity of central set of holes 215a. In some embodiments, the hole sizes of central set of holes 211a may be smaller than the hole sizes of central set of holes 215a. See e.g., FIG. 2A, FIG. 2B, and FIG. 2D.

In some embodiments, inner annular/ring set of holes 211b may be in direct linear and vertical alignment with inner annular/ring set of holes 215b (with a directly shared portion of fluid path 201), with inner most cylindrical annular/ring compartment(s) 205 disposed between inner annular/ring set of holes 211b and inner annular/ring set of holes 215b, wherein fluid entering inner annular/ring set of holes 211b will exit inner annular/ring set of holes 215b. In some embodiments, the hole sizes of inner annular/ring set of holes 211b may differ from the hole sizes of inner annular/ring set of holes 215b. In some embodiments, a quantity of inner annular/ring set of holes 211b may differ from a quantity of inner annular/ring set of holes 215b. In some embodiments, the hole sizes of inner annular/ring set of holes 211b may be smaller than the hole sizes of inner annular/ring set of holes 215b. See e.g., FIG. 2A, FIG. 2B, and FIG. 2D.

In some embodiments, middle annular/ring set of holes 211c may be in direct linear and vertical alignment with middle annular/ring set of holes 215c (with a directly shared portion of fluid path 201), with the middle annular/ring compartment(s) 205 disposed between middle annular/ring set of holes 211c and middle annular/ring set of holes 215c, wherein fluid entering middle annular/ring set of holes 211c will exit middle annular/ring set of holes 215c. In some embodiments, the hole sizes of middle annular/ring set of holes 211c may differ from the hole sizes of middle annular/ring set of holes 215c. In some embodiments, a quantity of middle annular/ring set of holes 211c may differ from a quantity of middle annular/ring set of holes 215c. In some embodiments, the hole sizes of middle annular/ring set of holes 211c may be larger than the hole sizes of middle annular/ring set of holes 215c. See e.g., FIG. 2A, FIG. 2B, and FIG. 2D.

In some embodiments, outer most annular/ring set of holes 211d may be in direct linear and vertical alignment with outer most annular/ring set of holes 215d (with a directly shared portion of fluid path 201), with the outer most annular/ring located compartment(s) 205 disposed between outer most annular/ring set of holes 211d and outer most annular/ring set of holes 215d, wherein fluid entering outer most annular/ring set of holes 211d will exit outer most annular/ring set of holes 215d. In some embodiments, the hole sizes of outer most annular/ring set of holes 211d may differ from the hole sizes of outer most annular/ring set of holes 215d. In some embodiments, a quantity of outer most annular/ring set of holes 211d may differ from a quantity of outer most annular/ring set of holes 215d. In some embodiments, the hole sizes of outer most annular/ring set of holes 211d may be larger than the hole sizes of outer most annular/ring set of holes 215d. See e.g., FIG. 2A, FIG. 2B, and FIG. 2D.

In some embodiments, there may be no such alignment between bottom holes 211 and upper holes 215. In some embodiments, there may be no such alignment between paired holes of a given bottom hole 211 and a given upper hole 215.

In some embodiments, top restrictor 207 may lead to a top exit chamber 208a of that sorbent cartridge 200. In some embodiments, the plurality of holes 215 (of top restrictor 207) may lead to top exit chamber 208a. In some embodiments, the plurality of holes 215 (of top restrictor 207) may be in communication with top exit chamber 208a. In some embodiments, each top most compartment 205 may empty out into top exit chamber 208a. In some embodiments, top exit chamber 208a may be a holding chamber of a predetermined and fixed volume for the fluid (used before the fluid finally exits that sorbent cartridge 200 through exit port 108b). See e.g., FIG. 2A and FIG. 2D. In some embodiments, top exit chamber 208a may be disposed opposite from bottom entry chamber 203b, with compartments 205 disposed between top exit chamber 208a and bottom entry chamber 203b. See e.g., FIG. 2A.

When the fluid has passed through the sorbent materials (the media) of the compartment(s) 205, the fluid achieves the top restrictor 207. The top restrictor 207 may comprise openings (e.g., holes 215) of varied, but fixed, sizes to moderate evenly the flow of fluid exiting the top most compartments 205. The fluid then enters top exit chamber 208a, which allows the fluid to pass out through the top restrictor 207 prior to exiting that sorbent cartridge 200. The fluid then exits through exit port 108b, designed to accommodate tubing/piping/plumbing as required/desired.

Note, while FIG. 2A may show sorbent cartridge 200 located with entry port 103a located vertically at a bottom and exit port 108b located vertically at a top; sorbent cartridge 200 may also be operated in a horizontal fashion, a diagonal fashion, or with entry port 103a located vertically at the top and exit port 108b located vertically at the bottom (i.e., in a configuration that is opposite to what is shown in FIG. 2A).

Figure 3A:
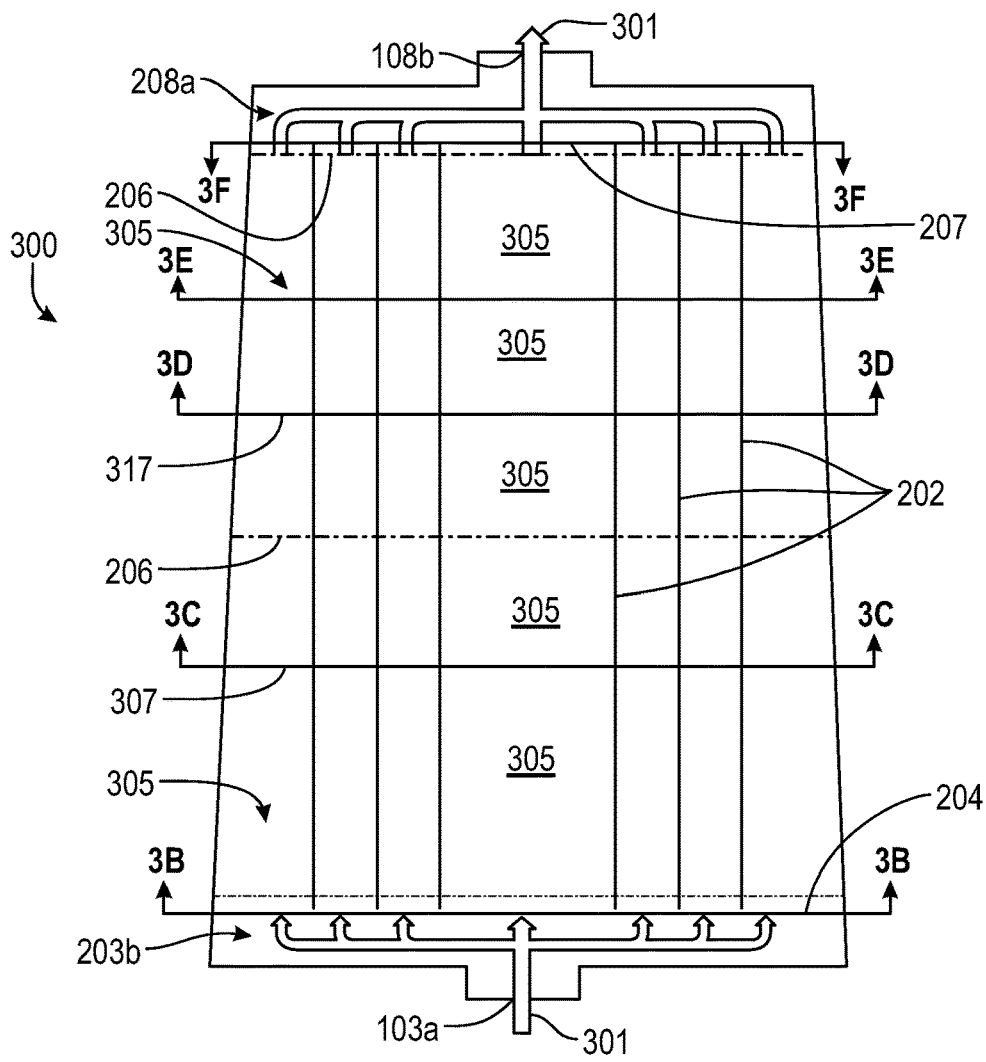
FIG. 3A may depict a schematic longitudinal cross-sectional diagram of a given sorbent cartridge.
Figures 3B, 3C:
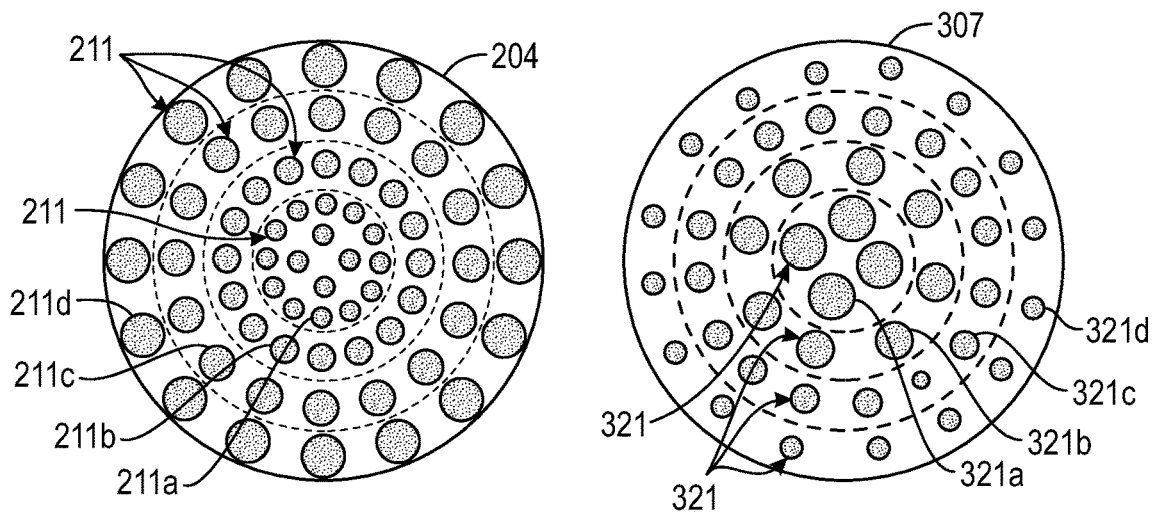
FIG. 3B may be a transverse-width cross-sectional diagram through sectional-line 3B-3B of FIG. 3A, showing a transverse-width cross-sectional portion of the sorbent cartridge of FIG. 3A.
FIG. 3C may be a transverse-width cross-sectional diagram through sectional-line 3C-3C of FIG. 3A, showing a transverse-width cross-sectional portion of the sorbent cartridge of FIG. 3A.
Figure 3D:
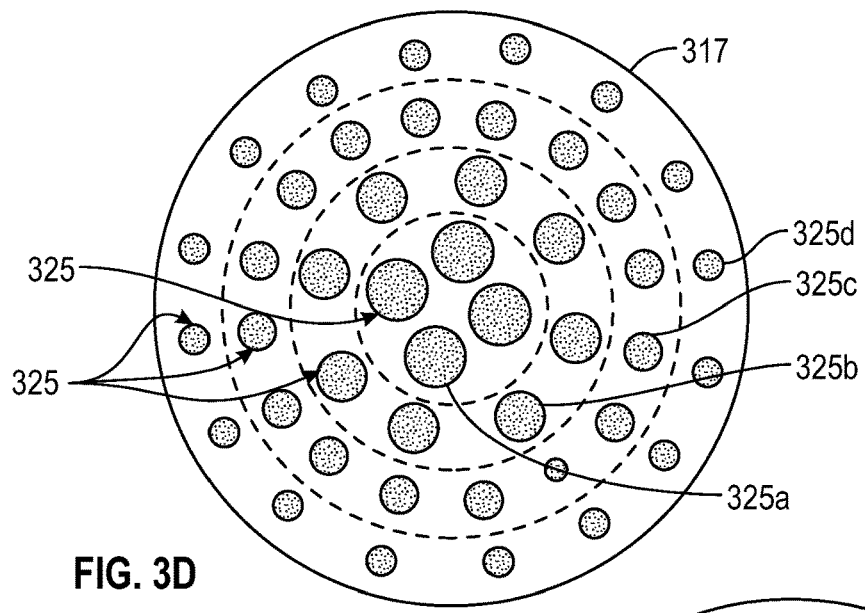
FIG. 3D may be a transverse-width cross-sectional diagram through sectional-line 3D-3D of FIG. 3A, showing a transverse-width cross-sectional portion of the sorbent cartridge of FIG. 3A.
Figure 3E:
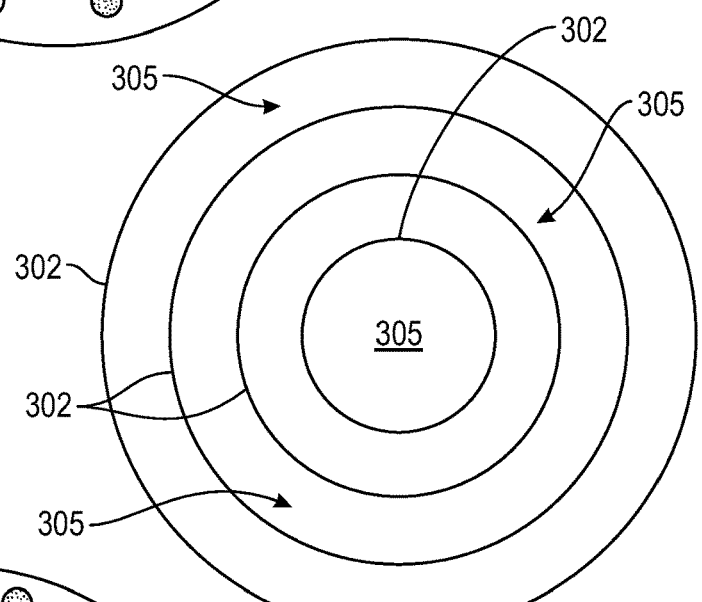
FIG. 3E may be a transverse-width cross-sectional diagram through sectional-line 3E-3E of FIG. 3A, showing a transverse-width cross-sectional portion of the sorbent cartridge of FIG. 3A.
Figure 3F:
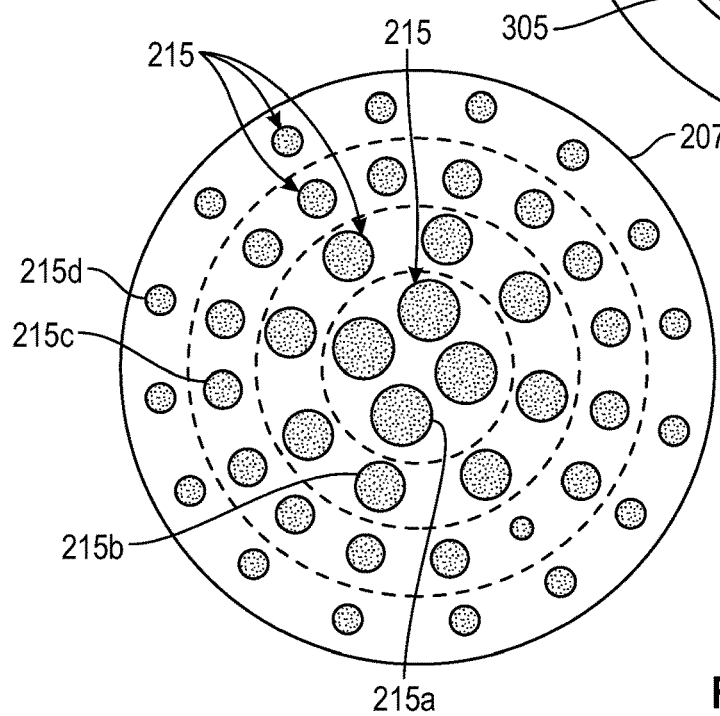
FIG. 3F may be a transverse-width cross-sectional diagram through sectional-line 3F-3F of FIG. 3A, showing a transverse-width cross-sectional portion of the sorbent cartridge of FIG. 3A.

FIG. 3A may depict a schematic longitudinal cross-sectional diagram of a sorbent cartridge 300. FIG. 3A may contain five transverse-width sectional-lines, namely, sectional-line 3B-3B (through bottom restrictor 204), sectional-line 3C-3C (through a restrictor 307), sectional-line 3D-3D (through a restrictor 317), sectional-line 3E-3E (through a portion of compartments 305), and sectional-line 3F-3F (through top restrictor 207). FIG. 3B may be a transverse-width cross-sectional diagram through sectional-line 3B-3B of FIG. 3A, showing a transverse-width cross-sectional portion of sorbent cartridge 300 through bottom restrictor 204. FIG. 3C may be a transverse-width cross-sectional diagram through sectional-line 3C-3C of FIG. 3A, showing a transverse-width cross-sectional portion of sorbent cartridge 300 through restrictor 307. FIG. 3D may be a transverse-width cross-sectional diagram through sectional-line 3D-3D of FIG. 3A, showing a transverse-width cross-sectional portion of sorbent cartridge 300 through restrictor 317. FIG. 3E may be a transverse-width cross-sectional diagram through sectional-line 3E-3E of FIG. 3A, showing a transverse-width cross-sectional portion through compartments 305 of sorbent cartridge 300. FIG. 3F may be a transverse-width cross-sectional diagram through sectional-line 3F-3F of FIG. 3A, showing a transverse-width cross-sectional portion of sorbent cartridge 300 through top restrictor 207. In some embodiments, sorbent cartridge 300 may be an example of the "segmented cartridge."

In some embodiments, sorbent cartridge 200 and sorbent cartridge 300 may be substantially similar both functionally and structurally, with a difference being that sorbent cartridge 300 may comprise one or more intermediary restrictors (such as, but not limited to, restrictor 307 and/or restrictor 317) disposed between bottom restrictor 204 and top restrictor 207. Compartments 205 in sorbent cartridge 200 and compartments 305 in sorbent cartridge 300 may both be vertically bound by vertical element(s) 202. Compartments 205 in sorbent cartridge 200 may be vertically capped (at a top and/or a bottom) by bottom restrictor 204, layer 206, and/or top restrictor 207; whereas, compartments 305 in sorbent cartridge 300 may be vertically capped (at a top and/or a bottom) by bottom restrictor 204, layer 206, restrictor 307, restrictor 317, and/or top restrictor 207. In some embodiments, sorbent cartridge 300 may share some components and/or structures with sorbent cartridge 200, such as, but not limited to: vertical element(s) 202, entry port 103a, exit port 108b, bottom entry chamber 203b, bottom restrictor 204, layer 206, top restrictor 207, top exit chamber 208a, holes 211, and holes 215.

In some embodiments, sorbent cartridge 300 may comprise one or more intermediary restrictors, such as, but not limited to, restrictor 307 and/or restrictor 317. In some embodiments, the intermediary restrictors of sorbent cartridge 300 may be disposed between bottom restrictor 204 and top restrictor 207. Because sorbent cartridge 300 may have one or more intermediary restrictors, sorbent cartridge 300 have a different fluid path from fluid path 201 for sorbent cartridge 200. The fluid path for sorbent cartridge 300 may be designated fluid path 301. Because compartments 305 of sorbent cartridge 300 may be capped by one or more intermediary restrictors, some compartments 305 may differ slightly from compartments 205 of sorbent cartridge 200 that are not capped by intermediary restrictors. However, some compartments 305 of sorbent cartridge 300 could be capped at both ends by layers 206 (or at one end by bottom restrictor 204 and a layer 206 at its other end or by top restrictor 207 at one end and a layer 206 and its other end) and thus those compartments 305 may be substantially similar to identical with compartments 205 in sorbent cartridge 200. In some embodiments, sorbent cartridge 300 may comprise compartments 305 and sometimes compartments 205. In some embodiments, the one or more intermediary restrictors (e.g., restrictor 307 and/or restrictor 317) may be placed within fluid path 301 to further modulate the flow of liquids through the adsorptive layers of the compartments 305/205.

In some embodiments, restrictor 307 may be a circular plate with a plurality of through holes 321. In some embodiments, the plurality of holes 321 of restrictor 307 may be of fixed (non-variable) and predetermined size(s). In some embodiments, the plurality of holes 321 of restrictor 307 may be different sizes (e.g., diameters). In some embodiments, holes 321 closer to an outside edge/exterior of restrictor 307 may be smaller than holes 321 located closer to a center of restrictor 307. In some embodiments, the plurality of holes 321 may be arranged into distinct sets of holes 321 corresponding to specific compartments 305. In some embodiments, for each different compartment 305 there may be a distinct set of holes 321 serving just that specific compartment 305. In some embodiments, for each different compartment 305 there may be a distinct set of holes 321 that lead to just that specific compartment 305. In some embodiments, for each different compartment 305 there may be a distinct set of holes 321 that are in communication with just that specific compartment 305. In some embodiments, restrictor 307 may have: a central region of a first set of holes 321a of a particular size (e.g., a first size) wherein these first set of holes 321a are in communication with centrally located compartments 305; an inner most annular/ring region of a second set of holes 321b of a particular size (e.g., a second size), wherein these second set of holes 321b are in communication with the inner most cylindrical annular/ring compartments 305; a middle annular/ring region of a third set of holes 321c of a particular size (e.g., a third size), wherein these third set of holes 321c are in communication with the middle cylindrical annular/ring compartments 305; and an outer most annular/ring region of a fourth set of holes 321d of a particular size (e.g., a fourth size), wherein these fourth set of holes 321d are in communication with the outer most cylindrical annular/ring compartments 305. In some embodiments, the first size, the second size, the third size, and the fourth size of the holes 321 may each be a different size (e.g., diameter) with respect to each other. In some embodiments, the first size may be larger than the second size, the second size may be larger than the third size, and the third size may be larger than the fourth size. In some embodiments, the first size (for central set of holes 321a) may be the largest size of the holes 321 of restrictor 307. In some embodiments, the fourth size (for outer most annular/ring set of holes 321d) may be the smallest size of the holes 321 of restrictor 307. See e.g., FIG. 3A and FIG. 3C.

In some embodiments, restrictor 317 may be a circular plate with a plurality of through holes 325. In some embodiments, the plurality of holes 325 of restrictor 317 may be of fixed (non-variable) and predetermined size(s). In some embodiments, the plurality of holes 325 of restrictor 317 may be different sizes (e.g., diameters). In some embodiments, holes 325 closer to an outside edge/exterior of restrictor 317 may be smaller than holes 325 located closer to a center of restrictor 317. In some embodiments, the plurality of holes 325 may be arranged into distinct sets of holes 325 corresponding to specific compartments 305. In some embodiments, for each different compartment 305 there may be a distinct set of holes 325 serving just that specific compartment 305. In some embodiments, for each different compartment 305 there may be a distinct set of holes 325 that lead to just that specific compartment 305. In some embodiments, for each different compartment 305 there may be a distinct set of holes 325 that are in communication with just that specific compartment 305. In some embodiments, restrictor 317 may have: a central region of a first set of holes 325a of a particular size (e.g., a first size) wherein these first set of holes 325a are in communication with centrally located compartments 305; an inner most annular/ring region of a second set of holes 325b of a particular size (e.g., a second size), wherein these second set of holes 325b are in communication with the inner most cylindrical annular/ring compartments 305; a middle annular/ring region of a third set of holes 325c of a particular size (e.g., a third size), wherein these third set of holes 325c are in communication with the middle cylindrical annular/ring compartments 305; and an outer most annular/ring region of a fourth set of holes 325d of a particular size (e.g., a fourth size), wherein these fourth set of holes 325d are in communication with the outer most cylindrical annular/ring compartments 305. In some embodiments, the first size, the second size, the third size, and the fourth size of the holes 325 may each be a different size (e.g., diameter) with respect to each other. In some embodiments, the first size may be larger than the second size, the second size may be larger than the third size, and the third size may be larger than the fourth size. In some embodiments, the first size (for central set of holes 325a) may be the largest size of the holes 325 of restrictor 317. In some embodiments, the fourth size (for outer most annular/ring set of holes 325d) may be the smallest size of the holes 325 of restrictor 317. See e.g., FIG. 3A and FIG. 3D.

In some embodiments, restrictor 307 may be substantially similar to identical with restrictor 317 in terms of function, structures, materials of construction, holes, hole placement, hole size, hole quantity, combinations thereof, and/or the like.

In some embodiments, restrictor 307 and restrictor 317 may be substantially similar to identical with top restrictor 207 in terms of function, structures, materials of construction, holes, hole placement, hole size, hole quantity, combinations thereof, and/or the like.

In some embodiments, central set of holes 211a may be in direct linear and vertical alignment with central set of holes 321a (with a directly shared portion of fluid path 301), with centrally located compartment(s) 305 disposed between central set of holes 211a and central set of holes 321a, wherein fluid entering central set of holes 211a will exit central set of holes 321a. In some embodiments, the hole sizes of central set of holes 211a may differ from the hole sizes of central set of holes 321a. In some embodiments, a quantity of central set of holes 211a may differ from a quantity of central set of holes 321a. In some embodiments, the hole sizes of central set of holes 211a may be smaller than the hole sizes of central set of holes 321a. See e.g., FIG. 3A, FIG. 3B, and FIG. 3C.

In some embodiments, inner annular/ring set of holes 211b may be in direct linear and vertical alignment with inner annular/ring set of holes 321b (with a directly shared portion of fluid path 301), with inner most cylindrical annular/ring compartment(s) 305 disposed between inner annular/ring set of holes 211b and inner annular/ring set of holes 321b, wherein fluid entering inner annular/ring set of holes 211b will exit inner annular/ring set of holes 321b. In some embodiments, the hole sizes of inner annular/ring set of holes 211b may differ from the hole sizes of inner annular/ring set of holes 321b. In some embodiments, a quantity of inner annular/ring set of holes 211b may differ from a quantity of inner annular/ring set of holes 321b. In some embodiments, the hole sizes of inner annular/ring set of holes 211b may be smaller than the hole sizes of inner annular/ring set of holes 321b. See e.g., FIG. 3A, FIG. 3B, and FIG. 3C.

In some embodiments, middle annular/ring set of holes 211c may be in direct linear and vertical alignment with middle annular/ring set of holes 321c (with a directly shared portion of fluid path 301), with the middle annular/ring compartment(s) 305 disposed between middle annular/ring set of holes 211c and middle annular/ring set of holes 321c, wherein fluid entering middle annular/ring set of holes 211c will exit middle annular/ring set of holes 321c. In some embodiments, the hole sizes of middle annular/ring set of holes 211c may differ from the hole sizes of middle annular/ring set of holes 321c. In some embodiments, a quantity of middle annular/ring set of holes 211c may differ from a quantity of middle annular/ring set of holes 321c. In some embodiments, the hole sizes of middle annular/ring set of holes 211c may be larger than the hole sizes of middle annular/ring set of holes 321c. See e.g., FIG. 3A, FIG. 3B, and FIG. 3C.

In some embodiments, outer most annular/ring set of holes 211d may be in direct linear and vertical alignment with outer most annular/ring set of holes 321d (with a directly shared portion of fluid path 301), with the outer most annular/ring located compartment(s) 305 disposed between outer most annular/ring set of holes 211d and outer most annular/ring set of holes 321d, wherein fluid entering outer most annular/ring set of holes 211d will exit outer most annular/ring set of holes 321d. In some embodiments, the hole sizes of outer most annular/ring set of holes 211d may differ from the hole sizes of outer most annular/ring set of holes 321d. In some embodiments, a quantity of outer most annular/ring set of holes 211d may differ from a quantity of outer most annular/ring set of holes 321d. In some embodiments, the hole sizes of outer most annular/ring set of holes 211d may be larger than the hole sizes of outer most annular/ring set of holes 321d. See e.g., FIG. 3A, FIG. 3B, and FIG. 3C.

In some embodiments, central set of holes 211a may be in direct linear and vertical alignment with central set of holes 325a (with a directly shared portion of fluid path 301), with centrally located compartment(s) 305 disposed between central set of holes 211a and central set of holes 325a, wherein fluid entering central set of holes 211a will exit central set of holes 325a. In some embodiments, the hole sizes of central set of holes 211a may differ from the hole sizes of central set of holes 325a. In some embodiments, a quantity of central set of holes 211a may differ from a quantity of central set of holes 325a. In some embodiments, the hole sizes of central set of holes 211a may be smaller than the hole sizes of central set of holes 325a. See e.g., FIG. 3A, FIG. 3B, and FIG. 3D.

In some embodiments, inner annular/ring set of holes 211b may be in direct linear and vertical alignment with inner annular/ring set of holes 325b (with a directly shared portion of fluid path 301), with inner most cylindrical annular/ring compartment(s) 305 disposed between inner annular/ring set of holes 211b and inner annular/ring set of holes 325b, wherein fluid entering inner annular/ring set of holes 211b will exit inner annular/ring set of holes 325b. In some embodiments, the hole sizes of inner annular/ring set of holes 211b may differ from the hole sizes of inner annular/ring set of holes 325b. In some embodiments, a quantity of inner annular/ring set of holes 211b may differ from a quantity of inner annular/ring set of holes 325b. In some embodiments, the hole sizes of inner annular/ring set of holes 211b may be smaller than the hole sizes of inner annular/ring set of holes 325b. See e.g., FIG. 3A, FIG. 3B, and FIG. 3D.

In some embodiments, middle annular/ring set of holes 211c may be in direct linear and vertical alignment with middle annular/ring set of holes 325c (with a directly shared portion of fluid path 301), with the middle annular/ring compartment(s) 305 disposed between middle annular/ring set of holes 211c and middle annular/ring set of holes 325c, wherein fluid entering middle annular/ring set of holes 211c will exit middle annular/ring set of holes 325c. In some embodiments, the hole sizes of middle annular/ring set of holes 211c may differ from the hole sizes of middle annular/ring set of holes 325c. In some embodiments, a quantity of middle annular/ring set of holes 211c may differ from a quantity of middle annular/ring set of holes 325c. In some embodiments, the hole sizes of middle annular/ring set of holes 211c may be larger than the hole sizes of middle annular/ring set of holes 325c. See e.g., FIG. 3A, FIG. 3B, and FIG. 3D.

In some embodiments, outer most annular/ring set of holes 211d may be in direct linear and vertical alignment with outer most annular/ring set of holes 325d (with a directly shared portion of fluid path 301), with the outer most annular/ring located compartment(s) 305 disposed between outer most annular/ring set of holes 211d and outer most annular/ring set of holes 325d, wherein fluid entering outer most annular/ring set of holes 211d will exit outer most annular/ring set of holes 325d. In some embodiments, the hole sizes of outer most annular/ring set of holes 211d may differ from the hole sizes of outer most annular/ring set of holes 325d. In some embodiments, a quantity of outer most annular/ring set of holes 211d may differ from a quantity of outer most annular/ring set of holes 325d. In some embodiments, the hole sizes of outer most annular/ring set of holes

211*d* may be larger than the hole sizes of outer most annular/ring set of holes 325*d*. See e.g., FIG. 3A, FIG. 3B, and FIG. 3D.

In some embodiments, restrictor 307 may be located beneath restrictor 317. See e.g., FIG. 3A.

Comparing restrictor 307 to restrictor 317, in some embodiments, central set of holes 321*a* may be in direct linear and vertical alignment with central set of holes 325*a* (with a directly shared portion of fluid path 301), with centrally located compartment(s) 305 disposed between central set of holes 321*a* and central set of holes 325*a*, wherein fluid entering central set of holes 321*a* will exit central set of holes 325*a*. In some embodiments, the hole sizes of central set of holes 321*a* may differ from the hole sizes of central set of holes 325*a*. In some embodiments, a quantity of central set of holes 321*a* may differ from a quantity of central set of holes 325*a*. In some embodiments, the hole sizes of central set of holes 321*a* may be smaller than the hole sizes of central set of holes 325*a*. See e.g., FIG. 3A, FIG. 3C, and FIG. 3D.

Comparing restrictor 307 to restrictor 317, in some embodiments, inner annular/ring set of holes 321*b* may be in direct linear and vertical alignment with inner annular/ring set of holes 325*b* (with a directly shared portion of fluid path 301), with inner most cylindrical annular/ring compartment(s) 305 disposed between inner annular/ring set of holes 321*b* and inner annular/ring set of holes 325*b*, wherein fluid entering inner annular/ring set of holes 321*b* will exit inner annular/ring set of holes 325*b*. In some embodiments, the hole sizes of inner annular/ring set of holes 321*b* may differ from the hole sizes of inner annular/ring set of holes 325*b*. In some embodiments, a quantity of inner annular/ring set of holes 321*b* may differ from a quantity of inner annular/ring set of holes 325*b*. In some embodiments, the hole sizes of inner annular/ring set of holes 321*b* may be smaller than the hole sizes of inner annular/ring set of holes 325*b*. See e.g., FIG. 3A, FIG. 3C, and FIG. 3D.

Comparing restrictor 307 to restrictor 317, in some embodiments, middle annular/ring set of holes 321*c* may be in direct linear and vertical alignment with middle annular/ring set of holes 325*c* (with a directly shared portion of fluid path 301), with the middle annular/ring compartment(s) 305 disposed between middle annular/ring set of holes 321*c* and middle annular/ring set of holes 325*c*, wherein fluid entering middle annular/ring set of holes 321*c* will exit middle annular/ring set of holes 325*c*. In some embodiments, the hole sizes of middle annular/ring set of holes 321*c* may differ from the hole sizes of middle annular/ring set of holes 325*c*. In some embodiments, a quantity of middle annular/ring set of holes 321*c* may differ from a quantity of middle annular/ring set of holes 325*c*. In some embodiments, the hole sizes of middle annular/ring set of holes 321*c* may be larger than the hole sizes of middle annular/ring set of holes 325*c*. See e.g., FIG. 3A, FIG. 3C, and FIG. 3D.

Comparing restrictor 307 to restrictor 317, in some embodiments, outer most annular/ring set of holes 321*d* may be in direct linear and vertical alignment with outer most annular/ring set of holes 325*d* (with a directly shared portion of fluid path 301), with the outer most annular/ring located compartment(s) 305 disposed between outer most annular/ring set of holes 321*d* and outer most annular/ring set of holes 325*d*, wherein fluid entering outer most annular/ring set of holes 321*d* will exit outer most annular/ring set of holes 325*d*. In some embodiments, the hole sizes of outer most annular/ring set of holes 321*d* may differ from the hole sizes of outer most annular/ring set of holes 325*d*. In some embodiments, a quantity of outer most annular/ring set of holes 321*d* may differ from a quantity of outer most annular/ring set of holes 325*d*. In some embodiments, the hole sizes of outer most annular/ring set of holes 321*d* may be larger than the hole sizes of outer most annular/ring set of holes 325*d*. See e.g., FIG. 3A, FIG. 3C, and FIG. 3D.

Note, while FIG. 3A may show sorbent cartridge 300 located with entry port 103*a* located vertically at a bottom and exit port 108*b* located vertically at a top; sorbent cartridge 300 may also be operated in a horizontal fashion, a diagonal fashion, or with entry port 103*a* located vertically at the top and exit port 108*b* located vertically at the bottom (i.e., in a configuration that is opposite to what is shown in FIG. 3A).

In some embodiments, sorbent cartridge 100, sorbent cartridge 200, and/or sorbent cartridge 300 may be described as comprising: a central casing, a bottom chamber (e.g., bottom entry chamber 103*b* and/or bottom entry chamber 203*b*), and a top chamber (e.g., top exit chamber 108*a* and/or top exit chamber 208*a*), and a region (configured for hosing the sorbent media) disposed between the bottom chamber and the top chamber and externally surrounded by the central casing. In some embodiments, the central casing may form external side walls of the given sorbent cartridge. In some embodiments, the central casing may be capped at both opposing ends, by the bottom cap and the top cap, respectively, such that the central casing, the bottom cap, and the top cap may substantially enclose a volume in a watertight manner. In some embodiments, the central casing may be the housing of the given sorbent cartridge. In some embodiments, the central housing may be the outermost vertical elements 102 and/or the outermost vertical elements 202. In some embodiments, the bottom chamber may occupy a first portion of the volume, wherein the bottom chamber may be capped by a bottom cap (e.g., a bottom portion of the bottom chamber) and by a bottom restrictor (e.g., bottom restrictor 104 and/or bottom restrictor 204). In some embodiments, the bottom restrictor may be disposed opposite from the bottom cap. In some embodiments, the side walls of the bottom chamber may be formed from a first portion (e.g., a bottom portion) of the central casing. In some embodiments, the bottom restrictor may be a first solid plate that may comprise a plurality of first holes (e.g., holes 211) that may pass entirely through the first solid plate. In some embodiments, the region that may be configured to house the sorbent media may house the sorbent media. In some embodiments, that region may occupy a second portion of the volume. In some embodiments, the plurality of first holes (of the bottom restrictor) may be in communication with that region and may lead into that region. In some embodiments, external side walls of that region may be formed from a second portion (e.g., a middle portion) of the central casing. In some embodiments, the top chamber may comprise a top restrictor. In some embodiments, the top restrictor may be a second solid plate that may comprise a plurality of second holes (e.g., holes 215) that may pass entirely through the second solid plate. In some embodiments, the top restrictor may be disposed opposite from the bottom restrictor, with the region that may be configured to house the sorbent media disposed between the bottom restrictor and the top restrictor. In some embodiments, the region that may be configured to house the sorbent media may be in communication with the plurality of second holes (of the top restrictor). In some embodiments, the top chamber may occupy a third portion (e.g., top portion) of the volume, wherein the top chamber may be capped by a top cap (e.g., a top portion of the top chamber) and by the top restrictor. In some embodiments, the top restrictor may be disposed opposite from the top cap.

In some embodiments, side walls of the top chamber may be formed from a third portion (e.g., a top portion) of the central casing.

In some embodiments, when the given sorbent cartridge 100, sorbent cartridge 200, and/or sorbent cartridge 300 may be in use, the dialysate stream fluid stream may enter the given sorbent cartridge at the bottom chamber (e.g., at the entry port 103*a* of the bottom chamber); then the dialysate stream fluid stream may be partially obstructed by the bottom restrictor before entering the region that may be configured to house the sorbent media; then the dialysate stream fluid stream may engage with the sorbent media; then the dialysate stream fluid stream may be partially obstructed by the top restrictor before entering the top chamber; and then the dialysate stream fluid stream may exit the given sorbent cartridge from the top chamber (e.g., through the exit port 108*b* of the top chamber).

In some embodiments, a given sorbent cartridge (e.g., sorbent cartridge 100, sorbent cartridge 200, and/or sorbent cartridge 300) may comprise a plurality of paired holes, wherein a given pair of holes selected from the plurality of paired holes may be a first hole (e.g., hole 211) selected from the plurality of first holes (e.g., holes 211) and a second hole (e.g., hole 215) selected from the plurality of second holes (e.g., holes 215); wherein each hole selected from the given pair of holes may be colinearly aligned with the other hole of that given pair of holes. In some embodiments, each hole of bottom restrictor 104 may be colinearly aligned and paired with a given hole from top restrictor 107. In some embodiments, each hole 211 may be colinearly aligned and paired with a given hole 215. In some embodiments, each hole selected from the given pair of holes may have a different diameter from the other hole of that given pair of holes. For example, and without limiting the scope of the present invention, each hole 211 may be colinearly aligned and paired with a given hole 215 and the diameter of each such paired hole 211 may be different from its paired hole 215.

In some embodiments, for a given sorbent cartridge (e.g., sorbent cartridge 100, sorbent cartridge 200, and/or sorbent cartridge 300) the plurality of first holes (e.g., holes 211) may have first holes (e.g., holes 211) located closer to a center of the bottom restrictor and may have different first holes (e.g., holes 211) located closer to an outer edge of the bottom restrictor; wherein the first holes (e.g., holes 211) located closer to the center of the bottom restrictor may be smaller in diameter than the different first holes (e.g., holes 211) located closer to the outer edge of the bottom restrictor. In some embodiments, for a given sorbent cartridge (e.g., sorbent cartridge 100, sorbent cartridge 200, and/or sorbent cartridge 300) the plurality of second holes (e.g., holes 215) may have second holes (e.g., holes 215) located closer to a center of the top restrictor and may have different second holes (e.g., holes 215) located closer to an outer edge of the top restrictor; wherein the second holes (e.g., holes 215) located closer to the center of the top restrictor may be larger in diameter than the different second holes (e.g., holes 215) located closer to the outer edge of the top restrictor. In some embodiments, the first holes (e.g., holes 211) that may be located closer to the center of the bottom restrictor may be in colinear alignment, on a one to one basis, with the second holes (e.g., holes 215) that are located closer to the center of top restrictor; wherein the different first holes (e.g., holes 211) that are located closer to the outer edge of the bottom restrictor may be in colinear alignment, on a one to one basis, with the different second holes (e.g., holes 215) that are located closer to the outer edge of the top restrictor. In some embodiments, each pair of holes, that may be in colinear alignment with each other, may have a different diameter from the other hole of that pair of holes, resulting in even flow of the dialysate stream fluid stream through the region that may be configured to house the sorbent media.

In some embodiments, for a given sorbent cartridge (e.g., sorbent cartridge 100, sorbent cartridge 200, and/or sorbent cartridge 300), the region that may be configured to house the sorbent media, may be a plurality of columns (e.g., columns 113, compartments 105, compartments 205, and/or compartments 305). In some embodiments, that plurality of columns may be bundled together within the central casing. In some embodiments, each column selected from the plurality of columns may be an elongate member that may be substantially hollow and configured to house the sorbent media. In some embodiments, at least one the columns selected from the plurality of columns may be housing the sorbent media. In some embodiments, the elongate member (e.g., of a given column) may be subdivided into at least two compartments (compartments 105, compartments 205, and/or compartments 305), wherein the at least two compartments may be arranged end to end with respect to each other. In some embodiments, each compartment selected from the at least two compartments may be configured to house the sorbent media. In some embodiments, at least one of the compartments selected from the at least two compartments may house the sorbent media. In some embodiments, a given sorbent cartridge (e.g., sorbent cartridge 100, sorbent cartridge 200, and/or sorbent cartridge 300), may comprise at least one layer (e.g., layer 106 and/or layer 206) that may be disposed between the at least two compartments, wherein the at least one layer may be comprised of a semi-permeable membrane that may be configured to allow passage of the dialysate stream fluid stream but that may block migration/movement of the sorbent media.

In some embodiments, for a given sorbent cartridge 100 the plurality of columns (e.g., columns 113) may be substantially shaped as a rectangular prism that may be substantially square or substantially rectangle in cross-section. See e.g., FIG. 1C, FIG. 1D, and FIG. 1E. In some embodiments, for a given sorbent cartridge 100, the elongate member (of a column 113) may be substantially shaped as a rectangular prism that may be substantially square or substantially rectangle in cross-section. See e.g., FIG. 1C, FIG. 1D, and FIG. 1E.

In some embodiments, a given sorbent cartridge 200 and/or a given sorbent cartridge 300 may comprise a plurality of cylindrical concentric members (e.g., vertical elements 202) that may run in a direction from the bottom restrictor to the top restrictor. In some embodiments, the plurality of cylindrical concentric members may be disposed between the bottom restrictor and the top restrictor forming a plurality of concentric compartments (e.g., compartments 205 and/or compartments 305) with a center most compartment that may be substantially cylindrical in shape and a plurality of cylindrical concentric annular shaped compartments around the center most compartment. See e.g., FIG. 2A, FIG. 2C, FIG. 3A, and FIG. 3E. In some embodiments, opposite ends of the plurality of cylindrical concentric members (e.g., vertical elements 202) may be touching the bottom restrictor and the top restrictor, respectively. In some embodiments, opposite ends of the plurality of cylindrical concentric members (e.g., vertical elements 202) may be attached to the bottom restrictor and to the top restrictor, respectively. See e.g., FIG. 2A and FIG. 3A. In some embodiments, each concentric compartment (compartment 205 and/or compartment 305) selected from the plurality of concentric compartments (compartments 205 and/or compartments 305) may be configured to house the sorbent media. In some embodiments, at least one concentric compartment (compartment 205 and/or compartment 305) selected from the plurality of concentric compartments (compartments 205 and/or compartments 305) may be configured to house the sorbent media. In some embodiments, at least one concentric compartment (compartment 205 and/or compartment 305) selected from the plurality of concentric compartments (compartments 205 and/or compartments 305) may house the sorbent media.

In some embodiments, for a given sorbent cartridge (e.g., sorbent cartridge 100) the central casing may be substantially a rectangular prism in shape (with rounded corners in some embodiments).

In some embodiments, for a given sorbent cartridge (e.g., sorbent cartridge 200, sorbent cartridge 300, and/or a sorbent cartridge 400) the central casing may be substantially cylindrical in shape. In some embodiments, for a given sorbent cartridge (e.g., sorbent cartridge 300 and/or sorbent cartridge 400) the central casing may be substantially conical (without a cone point/tip) in shape.

In some embodiments, a given sorbent cartridge (e.g., sorbent cartridge 100) may comprise at least one interim restrictor (e.g., restrictor 307 and/or restrictor 317). In some embodiments, the at least one interim restrictor may be disposed between the bottom restrictor and the top restrictor. In some embodiments, the at least one interim restrictor may be a third solid plate that may comprises a plurality of third holes (e.g., holes 321 and/or holes 325) that may pass entirely through the third solid plate. In some embodiments, the at least one interim restrictor (via its holes) may be configured to partially obstruct the dialysate stream fluid stream. See e.g., FIG. 3A, FIG. 3C, and FIG. 3D.

Figure 4A:
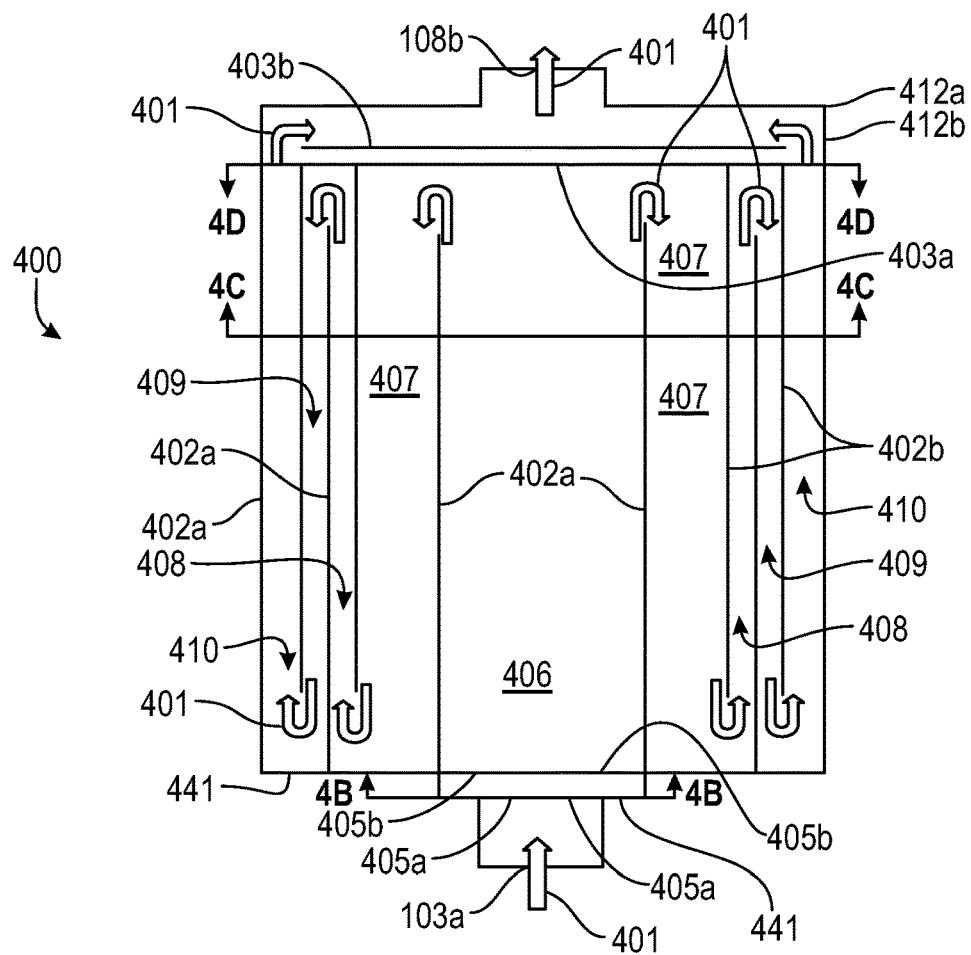
FIG. 4A may depict a schematic longitudinal cross-sectional diagram of a given sorbent cartridge.
Figure 4B:
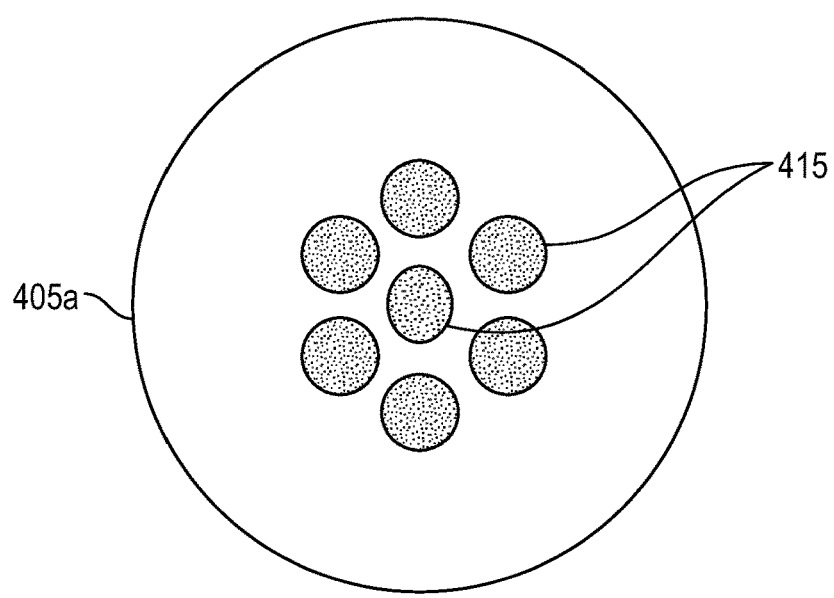
FIG. 4B may be a transverse-width cross-sectional diagram through sectional-line 4B-4B of FIG. 4A, showing a transverse-width cross-sectional portion of the sorbent cartridge of FIG. 4A.
Figure 4C:
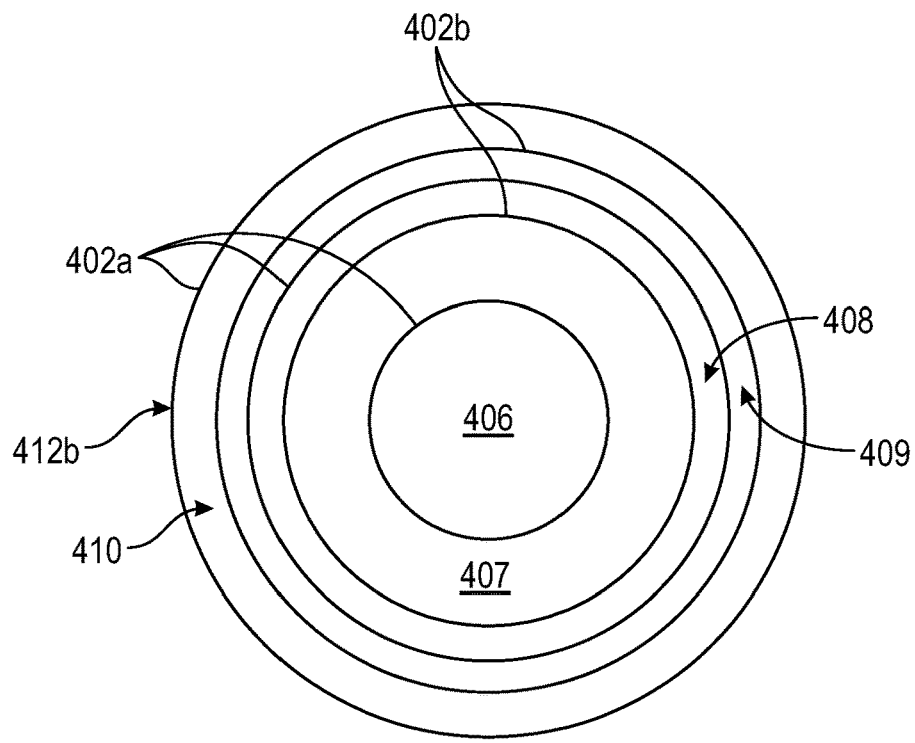
FIG. 4C may be a transverse-width cross-sectional diagram through sectional-line 4C-4C of FIG. 4A, showing a transverse-width cross-sectional portion of the sorbent cartridge of FIG. 4A.
Figure 4D:
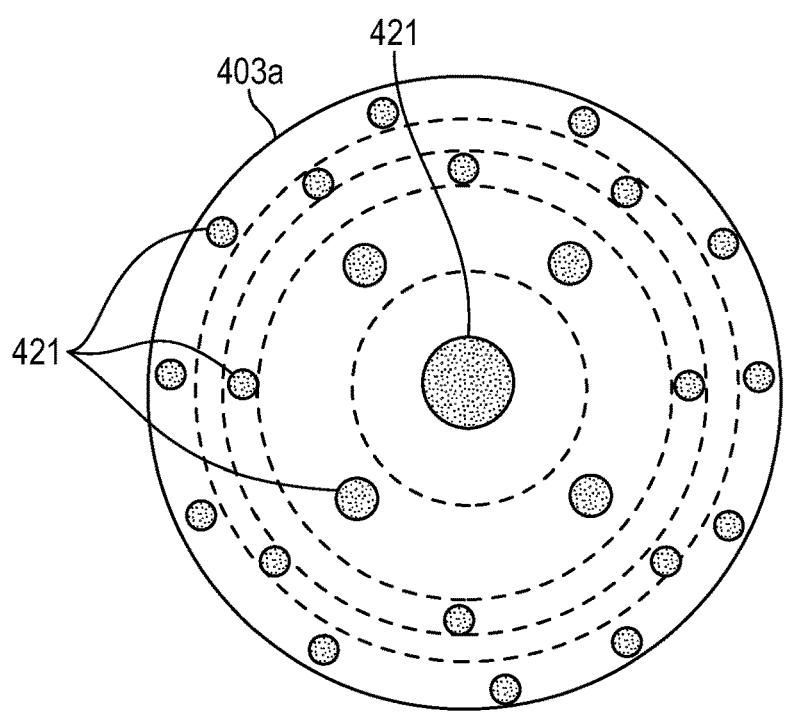
FIG. 4D may be a transverse-width cross-sectional diagram through sectional-line 4D-4D of FIG. 4A, showing a transverse-width cross-sectional portion of the sorbent cartridge of FIG. 4A.
Figure 4E:
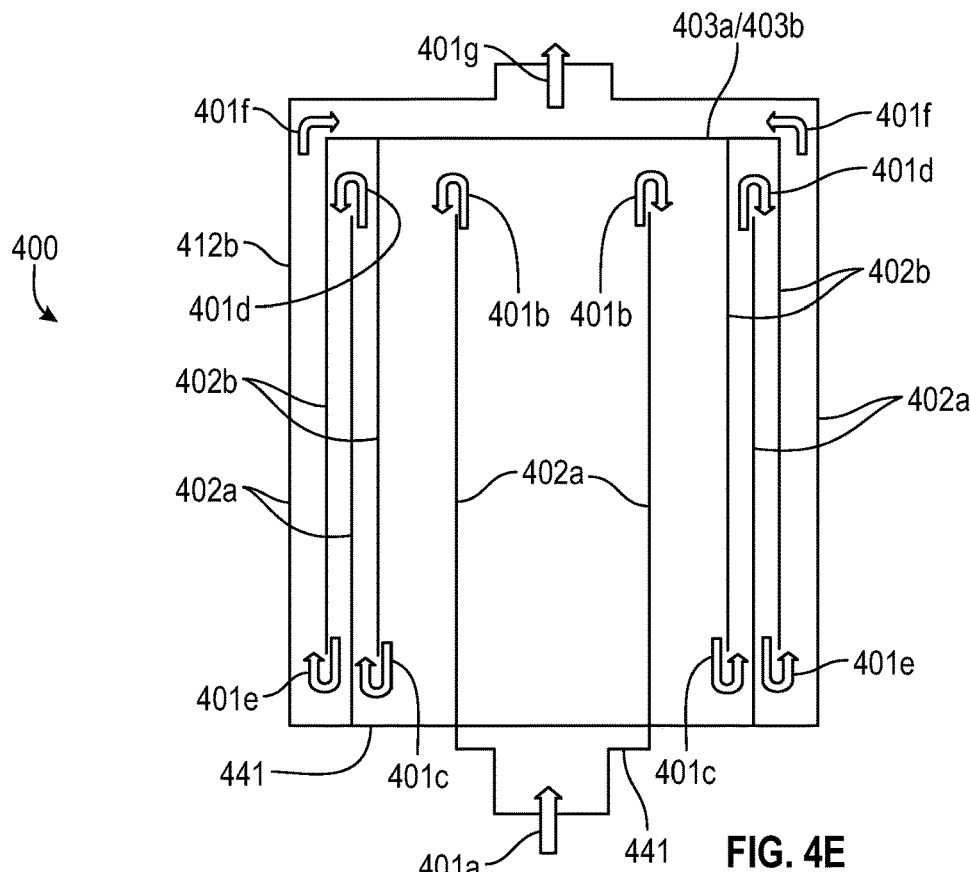
FIG. 4E may depict a schematic longitudinal cross-sectional diagram of the sorbent cartridge of FIG. 4A, with a focus on showing a fluid pathway through that sorbent cartridge.
Figure 4F:
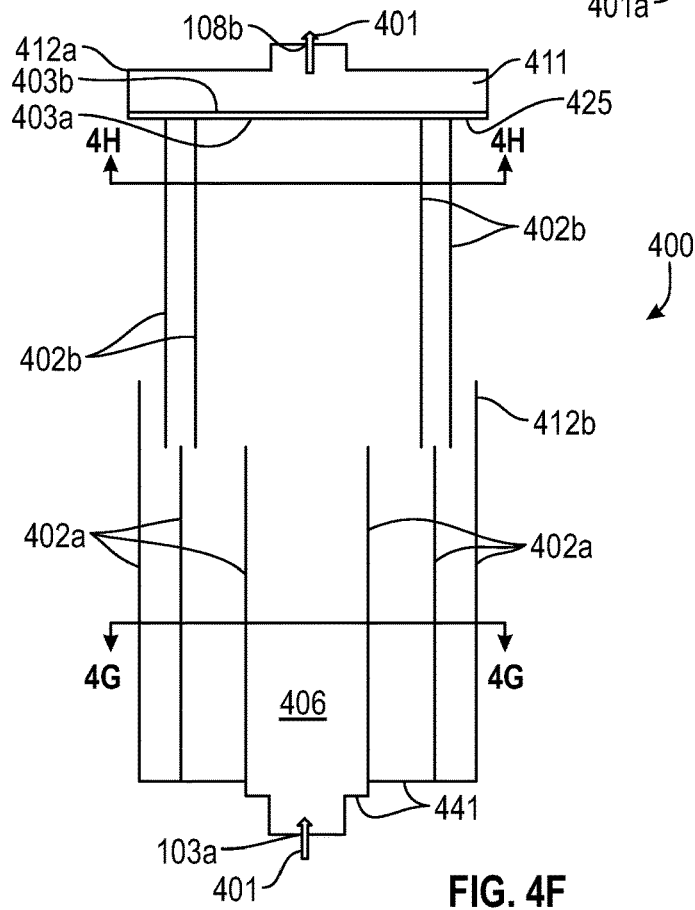
FIG. 4F may depict a schematic longitudinal cross-sectional diagram of the sorbent cartridge of FIG. 4A shown at least partially exploded.
Figure 4G:
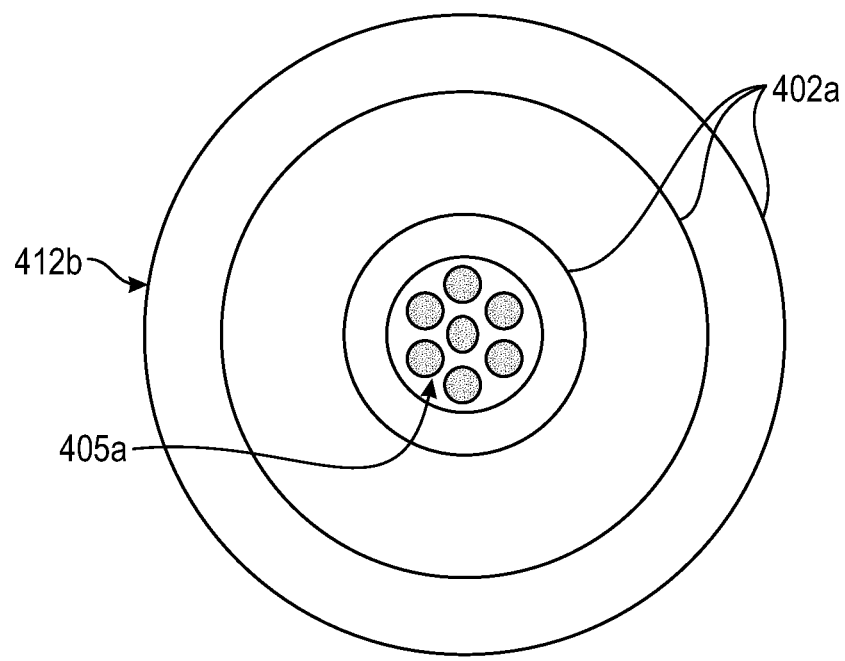
FIG. 4G may be a transverse-width cross-sectional diagram through sectional-line 4G-4G of FIG. 4F, showing a transverse-width cross-sectional portion of the sorbent cartridge of FIG. 4F.
Figure 4H:
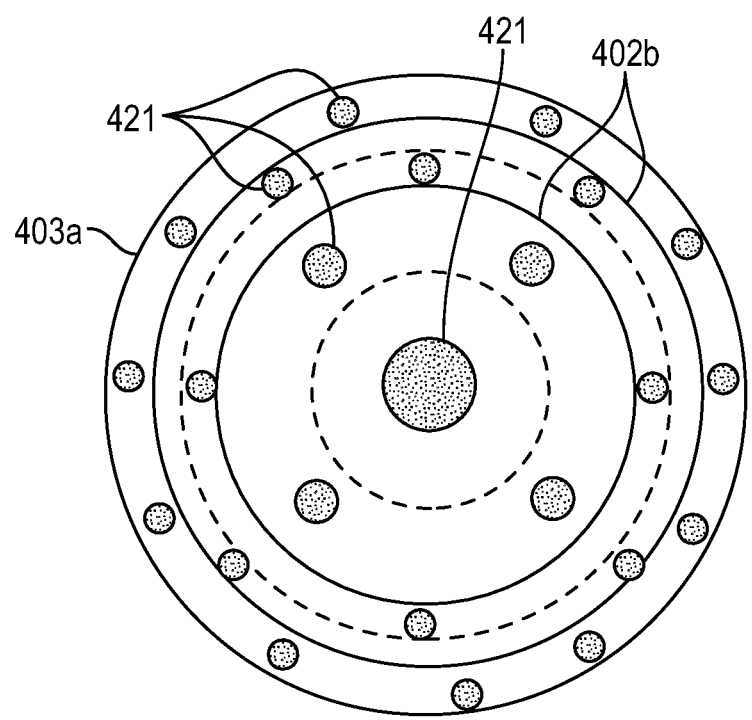
FIG. 4H may be a transverse-width cross-sectional diagram through sectional-line 4H-4H of FIG. 4F, showing a transverse-width cross-sectional portion of the sorbent cartridge of FIG. 4F.

FIG. 4A may depict a schematic longitudinal cross-sectional diagram of a sorbent cartridge 400. FIG. 4A may contain three transverse-width sectional-lines, namely, sectional-line 4B-4B (through bottom restrictor 405a), sectional-line 4C-4C (through a middle portion/region of sorbent cartridge 400), and sectional-line 4D-4D (through perforated surface 403a). FIG. 4B may be a transverse-width cross-sectional diagram through sectional-line 4B-4B of FIG. 4A, showing a transverse-width cross-sectional portion of sorbent cartridge 400 through bottom restrictor 405a. In some embodiments, bottom restrictor 405a may have at least one hole 415 through an otherwise solid member. In some embodiments, bottom restrictor 405a may have a plurality of holes 415 through an otherwise solid member. See e.g., FIG. 4B. FIG. 4C may be a transverse-width cross-sectional diagram through sectional-line 4C-4C of FIG. 4A, showing a transverse-width cross-sectional portion of the middle region of sorbent cartridge 400. FIG. 4D may be a transverse-width cross-sectional diagram through sectional-line 4D-4D of FIG. 4A, showing a transverse-width cross-sectional portion of sorbent cartridge 400 through perforated surface 403a. FIG. 4E may depict a schematic longitudinal cross-sectional diagram of sorbent cartridge 400, with a focus on showing a fluid pathway 401 through that sorbent cartridge 400. FIG. 4F may depict a schematic longitudinal cross-sectional diagram of sorbent cartridge 400 shown at least partially exploded. FIG. 4F may contain two transverse-width sectional-lines, namely, sectional-line 4G-4G (through a portion of alternating vertical concentric cylindrical elements 402a) and sectional-line 4H-4H (through a portion of alternating vertical concentric cylindrical elements 402b). FIG. 4G may be a transverse-width cross-sectional diagram through sectional-line 4G-4G of FIG. 4F, showing a transverse-width cross-sectional portion of sorbent cartridge 400 through a portion of alternating vertical concentric cylindrical elements 402a. FIG. 4H may be a transverse-width cross-sectional diagram through sectional-line 4H-4H of FIG. 4F, showing a transverse-width cross-sectional portion of sorbent cartridge 400 through a portion of alternating vertical concentric cylindrical elements 402b. In some embodiments, sorbent cartridge 400 may be an example of the "reversing-flow cartridge."

In some embodiments, fluid path 401 may refer to fluid pathways of the fluid (e.g., the dialysate stream) to, through, and/or out of sorbent cartridge 400. In some embodiments, fluid path 401a, fluid path 401b, fluid path 401c, fluid path 401d, fluid path 401e, fluid path 401f, and fluid path 401g may refer to specific regions of that fluid pathway. See e.g., FIG. 4A and FIG. 4E.

In some embodiments of sorbent cartridge 400, the fluid may first enter sorbent cartridge 400 at entry port 103a and into a bottom entry chamber; then hit bottom restrictor 405a (with at least one through hole 415) of that bottom entry chamber; then to semi-permeable membrane 405b. The fluid path up to this point may be designated by fluid path 401a in FIG. 4F. In some embodiments, semi-permeable membrane 405b may function substantially similarly to layers 106/206, i.e., may allow for fluid flow but may block media migration/movement.

In some embodiments, after the fluid passes past semi-permeable membrane 405b, the fluid may travel upwards through and into central cylindrical compartment 406. In some embodiments, when the fluid in compartment 406 reaches a top of compartment 406, e.g., at perforated surface 403a, that fluid may be blocked from entry into perforated surface 403a. In some embodiments, in normal use of sorbent cartridge 400, a back side of perforated surface 403a may have solid disk 403b attached to perforated surface 403a blocking any hole(s) 421 in perforated surface 403a. See e.g., FIG. 4A. In some embodiments, central cylindrical compartment 406 may be formed on its vertical sides by alternating vertical concentric cylindrical element 402a. In some embodiments, the alternating vertical concentric cylindrical element 402a that form the vertical sides of central cylindrical compartment 406 may not touch perforated surface 403a. In some embodiments, there may be a gap (or gaps) between perforated surface 403a and where the alternating vertical concentric cylindrical element(s) 402a ends. In some embodiments, the alternating vertical concentric cylindrical element(s) 402a may be attached to a bottom solid plate 441. In some embodiments, the alternating vertical concentric cylindrical element(s) 402a may originate from bottom solid plate 441. See e.g., FIG. 4F. In some embodiments, bottom solid plate 441 may not have holes or other means to permit fluid flow. In some embodiments, when the fluid reaches a top of compartment 406, the fluid may turn and enter compartment 407, wherein this fluid transition may be designated as fluid path 401b, see e.g., FIG. 4E. This may occur because of solid disk 403b blocking perforated surface 403a and due to the gaps between perforated surface 403a and the alternating vertical concentric cylindrical element(s) 402a.

In some embodiments, compartment 407 may be a cylindrical concentric annular/ring compartment that immediately surrounds compartment 406. See e.g., FIG. 4A and FIG. 4C. In some embodiments, vertical side walls of compartment 407 may be formed from the alternating vertical concentric cylindrical element 402a (that also surround compartment 406) and alternating vertical concentric cylindrical element 402b. In some embodiments, the alternating vertical concentric cylindrical element(s) 402b may originate from perforated surface 403a. In some embodiments, the alternating vertical concentric cylindrical element(s) 402b may be attached to perforated surface 403a. See e.g., FIG. 4F. In some embodiments, the alternating vertical concentric cylindrical element(s) 402b may not touch bottom solid plate 441. In some embodiments, there may be a gap (or gaps) between the alternating vertical concentric cylindrical element(s) 402b and bottom solid plate 441. See e.g., FIG. 4A and FIG. 4E.

In some embodiments, when the fluid in compartment 407 reaches a bottom of compartment 407 at bottom solid plate 441, the fluid may then turn and move upwards into compartment 408, wherein this fluid transition may be designated fluid path 401c. See e.g., FIG. 4E. In some embodiments, compartment 408 may be a cylindrical concentric annular/ring compartment that immediately surrounds compartment 407. See e.g., FIG. 4A and FIG. 4C. In some embodiments, vertical side walls of compartment 408 may be formed from the alternating vertical concentric cylindrical element 402b (that also surround compartment 407) and alternating vertical concentric cylindrical element 402a (note, not the same alternating vertical concentric cylindrical element 402a that surrounds compartment 406).

In some embodiments, when the fluid in compartment 408 reaches a top of compartment 408 at perforated surface 403a, the fluid may then turn and move downwards into compartment 409, wherein this fluid transition may be designated fluid path 401d. See e.g., FIG. 4E. In some embodiments, compartment 409 may be a cylindrical concentric annular/ring compartment that immediately surrounds compartment 408. See e.g., FIG. 4A and FIG. 4C. In some embodiments, vertical side walls of compartment 409 may be formed from the alternating vertical concentric cylindrical element 402a (that also surround compartment 408) and alternating vertical concentric cylindrical element 402b (note, not the same alternating vertical concentric cylindrical element 402b that surrounds compartment 407).

In some embodiments, when the fluid in compartment 409 reaches a bottom of compartment 409 at bottom solid plate 441a, the fluid may then turn and move upwards into compartment 410, wherein this fluid transition may be designated fluid path 401e. See e.g., FIG. 4E. In some embodiments, compartment 410 may be a cylindrical concentric annular/ring compartment that immediately surrounds compartment 409. See e.g., FIG. 4A and FIG. 4C. In some embodiments, vertical side walls of compartment 410 may be formed from the alternating vertical concentric cylindrical element 402b (that also surround compartment 409) and alternating vertical concentric cylindrical element 402a (an outer most cylindrical member of sorbent cartridge 400 which coincides with the main cylindrical housing member of sorbent cartridge 400). See e.g., FIG. 4A and FIG. 4E.

In some embodiments, when the fluid then reaches a top of compartment 410, the fluid may enter top chamber 411. See e.g., FIG. 4A. In some embodiments, the fluid transitioning from the top of compartment 410 and into top chamber 411 may be designated fluid path 401f. See e.g., FIG. 4E. In some embodiments, top chamber 411 may be separated from the top of compartment 410 by semi-permeable membrane 425. In some embodiments, semi-permeable membrane 425 may be an annular disk. In some embodiments, semi-permeable membrane 425 may function substantially similarly to layers 106/206/405b, i.e., may allow for fluid flow but may block media migration/movement. In some embodiments, top chamber 411 may be bounded on its outside by top cap 412a (at the top) and at the outer sides by outermost cylinder 412b. In some embodiments, top chamber 411 may exit/drain at exit port 108b. In some embodiments, the fluid exiting exit port 108b of top chamber 411 may be designated fluid path 401g. See e.g., FIG. 4E. In some embodiments, top cap 412a may be attached to the outermost cylinder 412b; wherein in some embodiments, a small step may be provided in the outermost cylindrical 412b to provide a support point for the top cap 412a. Note, in some embodiments, the outermost alternating vertical concentric cylindrical element 402a (e.g., surrounding compartment 410) may coincide with outermost cylinder 412b. See e.g., FIG. 4F.

In some embodiments, compartment 406, compartment 407, compartment 408, compartment 409, compartment 410, combinations thereof, and/or the like, may comprise/contain the media. In some embodiments, at least one compartment of sorbent cartridge 400 may comprise/contain various sorbent materials (i.e., the media), in an order and of a quantity to achieve the toxin adsorption and conversion required for dialysis.

In some embodiments, perforated surface 403a may have at least one hole 421 through an otherwise solid disk member. In some embodiments, perforated surface 403a may have a plurality of holes 421 through an otherwise solid disk member. See e.g., FIG. 4D. In some embodiments, any selection of hole(s) 421 through perforated surface 403a may be covered over and/or sealed by solid disk 403b. In some embodiments, solid disk 403b may be attached to perforated surface 403a to cover over and/or seal hole(s) 421 of perforated surface 403a. In some embodiments, perforated surface 403a may not have any through holes exposed to compartment 406, compartment 407, compartment 408, or compartment 409, and may just be a solid disk/plate member where associated with these compartments.

In some embodiments, where alternating vertical concentric cylindrical element(s) 402a are attached may be disposed opposite of where alternating vertical concentric cylindrical element(s) 402b are attached. See e.g., FIG. 4F.

In some embodiments, sorbent cartridge 400 may be configured for use in sorbent dialysis. In some embodiments, sorbent cartridge 400 may comprise: a central casing (e.g., outer most cylinder 112b or outermost alternating vertical concentric cylindrical element 402a), a bottom chamber (e.g., with entry port 103a and with bottom restrictor 405a), top chamber 411, and a plurality of concentric compartments (e.g., compartment 406, compartment 407, compartment 408, compartment 409, and compartment 410). See e.g., FIG. 4A.

In some embodiments, the central casing may form external side walls of sorbent cartridge 400. In some embodiments, the central casing may be capped at both opposing ends, by a bottom cap (e.g., by bottom solid plate 441) and top cap 412a, respectively, such that the central casing, the bottom cap, and the top cap may substantially enclose a volume in a water-tight manner. See e.g., FIG. 4A.

In some embodiments, the bottom chamber may occupy a first portion (e.g., bottom portion) of the volume, wherein the bottom chamber may be capped by the bottom cap (e.g., bottom solid plate 441) and by bottom restrictor 405a. In some embodiments, bottom restrictor 405a may be disposed opposite from the bottom cap; wherein side walls of the bottom chamber may be formed from a first portion (e.g., a bottom portion) of the central casing. In some embodiments, bottom restrictor 405a may be a first solid plate that may comprises a plurality of first holes (e.g., holes 415) that may pass entirely through that first solid plate (bottom restrictor 405a). See e.g., FIG. 4A and FIG. 4B.

In some embodiments, the plurality of concentric compartments (e.g., compartment 406, compartment 407, compartment 408, compartment 409, and compartment 410) may be configured to house the sorbent media. In some embodiments, at least one of the concentric compartments (e.g., compartment 406, compartment 407, compartment 408, compartment 409, and compartment 410) selected from the plurality of concentric compartments (e.g., compartment 406, compartment 407, compartment 408, compartment 409, and compartment 410) may house the sorbent media.

In some embodiments, the plurality of concentric compartments (e.g., compartment 406, compartment 407, compartment 408, compartment 409, and compartment 410) may occupy a second portion (e.g., a middle portion) of the volume (of sorbent cartridge 400). In some embodiments, the plurality of concentric compartments may comprise a center most compartment 406 that may be substantially cylindrical in shape and a plurality of cylindrical concentric annular shaped compartments (e.g., compartment 407, compartment 408, compartment 409, and compartment 410) around the center most compartment 406.

In some embodiments, the plurality of first holes (e.g., holes 415) may be in fluid communication with center most compartment 406 and may lead into the center most compartment 406. In some embodiments, the plurality of first holes (e.g., holes 415) may first lead to semi-permeable membrane 405b before entering center most compartment 406. In some embodiments, semi-permeable membrane 405b may prevent sorbent media from entering the bottom chamber and/or from entering bottom restrictor 405a; however, semi-permeable membrane 405b may permit dialysate stream flow. In some embodiments, external side walls of the plurality of concentric compartments may be formed from a second portion (e.g., a middle portion) of the central casing (e.g., outer most cylinder 112b or outermost alternating vertical concentric cylindrical element 402a). In some embodiments, internal side walls (e.g., interior alternating vertical concentric cylindrical element 402a/402b) of the plurality of concentric compartments may be formed from a plurality of cylindrical concentric members (e.g., interior alternating vertical concentric cylindrical element 402a/402b) that may run in a direction from the bottom cap towards the top cap 412a. In some embodiments, the plurality of cylindrical concentric members may be disposed between the bottom cap and a top member (e.g., perforated surface 403a and/or solid disk 403b) of sorbent cartridge 400. See e.g., FIG. 4A and FIG. 4B.

In some embodiments, some of the plurality of cylindrical concentric members (e.g., alternating vertical concentric cylindrical elements 402a) are attached to the bottom cap (e.g., bottom solid plate 441) with a first gap at the top member (e.g., perforated surface 403a); wherein a remaining of the plurality of cylindrical concentric members (e.g., alternating vertical concentric cylindrical elements 402b) are attached to the top member (e.g., perforated surface 403a) with a second gap at the bottom cap (e.g., bottom solid plate 441).

For example and without limiting the scope of the present invention, alternating vertical concentric cylindrical elements 402a may not be touching the top member (e.g., perforated surface 403a), providing/creating the first gap; and alternating vertical concentric cylindrical elements 402b may not be touching the bottom cap (e.g., bottom solid plate 441), providing/creating the second gap. For example and without limiting the scope of the present invention, at least some portion of alternating vertical concentric cylindrical elements 402a may not be touching the top member (e.g., perforated surface 403a), providing/creating the first gap; and at least some portion of alternating vertical concentric cylindrical elements 402b may not be touching the bottom cap (e.g., bottom solid plate 441), providing/creating the second gap. In some embodiments, the first gap and the second gap may allow flow of the dialysate stream into different regions/portions/compartments. See e.g., FIG. 4A, FIG. 4E, and FIG. 4F.

In some embodiments, with respect to a transverse cross-section through a middle region of sorbent cartridge 400, that transverse cross-section, from an outside to a center of sorbent cartridge 400, may encounter: first the central casing, then an outer most concentric annular compartment 410 selected from the plurality of cylindrical concentric annular shaped compartments; then one of the cylindrical concentric members (e.g., alternating vertical concentric cylindrical element 402b) that is attached to the top member; then a next concentric annular compartment 409 selected from the plurality of cylindrical concentric annular shaped compartments; then one of the cylindrical concentric members (e.g., alternating vertical concentric cylindrical element 402a) that is attached to the bottom cap; then a further concentric annular compartment 408 selected from the plurality of cylindrical concentric annular shaped compartments; then a second of the cylindrical concentric members (e.g., alternating vertical concentric cylindrical element 402b) that is attached to the top member; then an inner concentric annular compartment 407 selected from the plurality of cylindrical concentric annular shaped compartments; then a second of the cylindrical member (e.g., alternating vertical concentric cylindrical element 402a) that is attached to the bottom cap; and then the center most compartment 406. See e.g., FIG. 4A, FIG. 4E, and FIG. 4F.

In some embodiments, top chamber 411 may occupy a third portion (e.g., top portion) of the volume (of sorbent cartridge 400), wherein the top chamber may be capped by top cap 412a and by the top member (e.g., perforated surface 403a and/or solid disk 403b). In some embodiments, the top member may be disposed opposite from top cap 412a; wherein side walls of the top chamber 411 may be formed from a third portion (e.g., a top portion) of the central casing (e.g., outermost cylinder 112b). See e.g., FIG. 4A.

In some embodiments, sorbent cartridge 400 prior to use in sorbent dialysis, holes (e.g., holes 421) in perforated surface 403a may be used to load the sorbent media into compartments (e.g., compartment 406, compartment 407, compartment 408, compartment 409, and compartment 410) of sorbent cartridge 400.

In some embodiments, perforated surface 403a and solid disk 403b may have diameters that are less than an inside diameter of outermost cylinder 412b. See e.g., FIG. 4A and FIG. 4E. In some embodiments, when sorbent cartridge 400 may be in use for sorbent dialysis, there may no holes for fluid movement in the top member, but fluid may move around peripheral edges of the top member. In some embodiments, when sorbent cartridge 400 may be in use for sorbent dialysis, solid disk 403b may block any holes (e.g., holes 421) in perforated surface 403a, and fluid may pass around peripheral edges of perforated surface 403a and solid disk 403b, and fluid may pass around peripheral edges of perforated surface 403a.

Whereas in other embodiments, a diameter of perforated surface 403a may extend out to the inside diameter of outermost cylinder 412b, in which case the diameter of solid disk 403b may less than the diameter of perforated surface 403a, such that solid disk 403b covers all holes 421 of perforated surface 403a except for the outer ring of holes 421 in perforated surface 403a. In some embodiments, solid disk 403b may only cover holes 421 of perforated surface 403a after the sorbent media has been added through holes 421 of perforated surface 403a into compartments (such as, but not limited to, compartment 406, compartment 407, compartment 408, and/or compartment 409).

In some embodiments, when sorbent cartridge 400 may be in use for sorbent dialysis, the dialysate stream fluid stream may enter sorbent cartridge 400 at the bottom chamber (e.g., via entry port 103a); then the dialysate stream fluid stream may be partially obstructed by bottom restrictor 405a before entering the center most compartment 406; then the dialysate stream fluid stream may change (e.g., reverse) direction upon entering the inner concentric annular compartment 407; then the dialysate stream fluid stream may change (e.g., reverse) direction upon entering the further concentric annular compartment 408; then the dialysate stream fluid stream may change (e.g., reverse) direction upon entering the next concentric annular compartment 409; then the dialysate stream fluid stream may change (e.g., reverse) direction upon entering the outer most concentric annular compartment 410; then the dialysate stream fluid stream may enter top chamber 411; and then the dialysate stream fluid stream exits sorbent cartridge 400 from top chamber 411 (e.g., via exit port 108b); wherein as the dialysate stream fluid stream flows through the plurality of concentric compartments, the dialysate stream fluid stream may engage with the sorbent media that may be housed in at least one of the compartments. In some embodiments, the dialysate stream fluid stream, as it passes through sorbent cartridge 400, may go through at least four reversals in fluid flow direction. In some embodiments, the first gaps and/or the second gaps have predetermined and different sizes configured for substantially even fluid flows through sorbent media within sorbent cartridge 400. See e.g., FIG. 4E.

FIG. 5A may depict a schematic longitudinal cross-sectional diagram of a system of at least two sorbent cartridges (e.g., cartridge 521 and sorbent cartridge 200) arranged in series with respect to each other. In some embodiments, in FIG. 5A, a fluid path 501 may be the fluid passing through two or more serially connected cartridges. In some embodiments, cartridge 521 may be attached to sorbent cartridge 200. In some embodiments, cartridge 521 may be removably attached to sorbent cartridge 200. In some embodiments, cartridge 521 may be indirectly attached to sorbent cartridge 200, with one or more tubing/piping elements and/or valves disposed between cartridge 521 and sorbent cartridge 200; and wherein the one or more tubing/piping element and/or the valves may be in-line with the fluid path 501. In some embodiments, cartridge 521 may be directly attached to sorbent cartridge 200, with an exit port of cartridge 521 running directly into entry port 103a of sorbent cartridge 200. In some embodiments, cartridge 521 may be a disposable/single use filtration/sorbent cartridge. In some embodiments, cartridge 521 may be a prior art filtration/sorbent cartridge. In some embodiments, cartridge 521 may be one or more of: a sorbent cartridge, a disposable cartridge, a pre-filter, a filter, a filtration cartridge, sorbent cartridge 100, sorbent cartridge 200, sorbent cartridge 300, sorbent cartridge 400, combinations thereof, and/or the like.

In some embodiments, sorbent cartridge 200 in FIG. 5A may be replaced with sorbent cartridge 100, sorbent cartridge 300, sorbent cartridge 400, or sorbent cartridge 521.

FIG. 5B may depict a schematic block diagram of a system of at least two sorbent cartridges (e.g., a first cartridge 531 and a second cartridge 533) arranged in series with respect to each other. In some embodiments, FIG. 5B may depict a schematic block diagram of a system of at least three sorbent cartridges (e.g., first cartridge 531, second cartridge 533, and a third cartridge 535) arranged in series with respect to each other. In some embodiments, first cartridge 531 may be selected from: sorbent cartridge 100, sorbent cartridge 200, sorbent cartridge 300, sorbent cartridge 400, or sorbent cartridge 521. In some embodiments, second cartridge 533 may be selected from: sorbent cartridge 100, sorbent cartridge 200, sorbent cartridge 300, sorbent cartridge 400, or sorbent cartridge 521. In some embodiments, third cartridge 535 may be selected from: sorbent cartridge 100, sorbent cartridge 200, sorbent cartridge 300, sorbent cartridge 400, or sorbent cartridge 521.

In some embodiments, sorbent cartridge 100, sorbent cartridge 200, sorbent cartridge 300, sorbent cartridge 400, sorbent cartridge 521, first cartridge 531, second cartridge 533, third cartridge 535, combinations thereof, and/or the like, may be configured for use in sorbent dialysis.

Note the restrictors discussed herein may be used to more evenly distribute fluid flows through the sorbent cartridges discussed herein, which in turn may maximize the fluid's exposure to the sorbent media that may reside in a given compartment of the given sorbent cartridge, as discussed above.

In some embodiments, sorbent cartridge 100, sorbent cartridge 200, sorbent cartridge 300, sorbent cartridge 400, sorbent cartridge 521, first cartridge 531, second cartridge 533, and/or third cartridge 535, combinations thereof, and/or the like, may be reusable.

In some embodiments, sorbent cartridge 100, sorbent cartridge 200, sorbent cartridge 300, sorbent cartridge 400, sorbent cartridge 521, first cartridge 531, second cartridge 533, and/or third cartridge 535, combinations thereof, and/or the like, may be single use (disposable).

In some embodiments, the cartridges discussed herein may provide for one or more of: mechanical filtration, chemical filtration, biological filtration, combinations thereof, and/or the like.

In some embodiments, the compartments of the cartridges discussed herein may provide for one or more of: mechanical filtration, chemical filtration, biological filtration, combinations thereof, and/or the like.

In some embodiments, the media discussed herein may provide for one or more of: mechanical filtration, chemical filtration, biological filtration, combinations thereof, and/or the like.

In some embodiments, the media for use in a given compartment of a given cartridge may be substantially enclosed/sealed within its own perforated/semi-permeable: bag, envelope, container, combinations thereof, and/or the like—that permits fluid flow but restricts movement/migration of the media.

In some embodiments, a given sorbent cartridge discussed herein may be readily/substantially portable/mobile. In some embodiments, a given sorbent cartridge discussed herein may be configured to be readily/substantially portable/mobile by a single person, without any additional tools/carrying devices.

In some embodiments, components, parts, structures, elements, members, combinations thereof, and/or the like of the various sorbent cartridges discussed herein may be manufactured by one or more of the following processes: injection molding, extrusion, 3D (three dimensional) printing, stamping, machining, milling, die cutting, cutting, heat shaping/bending, combinations thereof, and/or the like.

In some embodiments, components, parts, structures, elements, members, combinations thereof, and/or the like of the various sorbent cartridges discussed herein may be joined together (attached together) by one or more of the following: welding, solvent bonding, ultrasonic welding, heat welding, chemical adhesive, mechanical fastener, friction fit, snap fit, threading, combinations thereof, and/or the like.

Devices (e.g., sorbent cartridges), systems, and methods for even fluid dispersion through higher density media have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A sorbent cartridge configured for use in sorbent dialysis, the sorbent cartridge comprising:
   a central casing that forms external side walls of the sorbent cartridge, wherein the central casing is capped at both opposing ends, by a bottom cap and a top cap, respectively, such that the central casing, the bottom cap, and the top cap substantially encloses a volume in a watertight manner;
   a bottom chamber that occupies a first portion of the volume, wherein the bottom chamber is capped by the bottom cap and by a bottom restrictor; wherein the bottom restrictor is disposed opposite from the bottom cap; wherein side walls of the bottom chamber are formed from a first portion of the central casing;
   the bottom restrictor is a first solid plate that comprises a plurality of first holes that pass entirely through the first solid plate; wherein the plurality of first holes has first holes located closer to a center of the bottom restrictor and has different first holes located closer to an outer edge of the bottom restrictor; wherein the first holes located closer to the center of the bottom restrictor are smaller in diameter than the different first holes located closer to the outer edge of the bottom restrictor;
   a region configured to house sorbent media, wherein the region houses the sorbent media, wherein the region occupies a second portion of the volume; wherein the plurality of first holes are in communication with the region and lead into the region; wherein external side walls of the region are formed from a second portion of the central casing;
   a top restrictor that is a second solid plate that comprises a plurality of second holes that pass entirely through the second solid plate; wherein the top restrictor is disposed opposite from the bottom restrictor; wherein the region is in communication with the plurality of second holes; wherein the plurality of second holes has second holes located closer to a center of the top restrictor and has different second holes located closer to an outer edge of the top restrictor; wherein the second holes located closer to the center of the top restrictor are larger in diameter than the different second holes located closer to the outer edge of the top restrictor;
   a top chamber that occupies a third portion of the volume, wherein the top chamber is capped by the top cap and by the top restrictor; wherein the top restrictor is disposed opposite from the top cap; wherein side walls of the top chamber are formed from a third portion of the central casing;
   wherein in use, a dialysate fluid stream enters the sorbent cartridge at the bottom chamber; then is partially obstructed by the bottom restrictor before entering the region; then engages with the sorbent media; then is partially obstructed by the top restrictor before entering the top chamber; and then exits the sorbent cartridge from the top chamber.

2. The sorbent cartridge according to claim 1, wherein the sorbent cartridge comprises a plurality of paired holes, wherein a given pair of holes selected from the plurality of paired holes is a first hole selected from the plurality of first holes and a second hole selected from the plurality of second holes; wherein each hole selected from the given pair of holes is colinearly aligned with the other hole of that given pair of holes.

3. The sorbent cartridge according to claim 2, wherein each hole selected from the given pair of holes has a different diameter from the other hole of that given pair of holes.

4. The sorbent cartridge according to claim 1, wherein the first holes that are located closer to the center of the bottom restrictor are in colinear alignment, on a one to one basis, with the second holes that are located closer to the center of top restrictor; wherein the different first holes that are located closer to the outer edge of the bottom restrictor are in colinear alignment, on a one to one basis, with the different second holes that are located closer to the outer edge of the top restrictor.

5. The sorbent cartridge according to claim 4, wherein each pair of holes, that are in colinear alignment with each other, has a different diameter from the other hole of that pair of holes, resulting in even flow of the dialysate fluid stream through the region.

6. The sorbent cartridge according to claim 1, wherein the region is a plurality of columns, wherein the plurality of columns are bundled together within the central casing.

7. The sorbent cartridge according to claim 6, wherein the plurality of columns are substantially shaped as a rectangular prism that is substantially square or substantially rectangular in cross-section.

8. The sorbent cartridge according to claim 6, wherein each column selected from the plurality of columns is an elongate member that is substantially hollow and configured to house at least some of the sorbent media.

9. The sorbent cartridge according to claim 8, wherein the elongate member is substantially shaped as a rectangular prism that is substantially square or substantially rectangular in cross-section.

10. The sorbent cartridge according to claim 8, wherein the elongate member is subdivided into at least two compartments, wherein the at least two compartments are arranged end to end with respect to each other.

11. The sorbent cartridge according to claim 10, wherein each compartment selected from the at least two compartments is configured to house at least a portion of the sorbent media.

12. The sorbent cartridge according to claim 10, wherein the sorbent cartridge comprises at least one layer that is disposed between the at least two compartments, wherein the at least one layer is comprised of a semi-permeable membrane that is configured to allow passage of the dialysate fluid stream but that blocks migration of the sorbent media.

13. The sorbent cartridge according to claim 1, the region comprises a plurality of cylindrical concentric members that run in a direction from the bottom restrictor to the top restrictor; wherein the plurality of cylindrical concentric members are disposed between the bottom restrictor and the top restrictor forming a plurality of concentric compartments with a center most compartment that is substantially cylindrical in shape and a plurality of cylindrical concentric annular shaped compartments around the center most compartment.

14. The sorbent cartridge according to claim 13, wherein opposite ends of the plurality of cylindrical concentric members are touching the bottom restrictor and the top restrictor, respectively.

15. The sorbent cartridge according to claim 13, wherein each concentric compartment selected from the plurality of concentric compartments is configured to house at least some of the sorbent media.

16. The sorbent cartridge according to claim 13, wherein the sorbent cartridge comprises at least one interim restrictor; wherein the at least one interim restrictor is disposed between the bottom restrictor and the top restrictor; wherein the at least one interim restrictor is a third solid plate that comprises a plurality of third holes that pass entirely through the third solid plate; wherein the at least one interim restrictor is configured to partially obstruct the dialysate fluid stream.

17. The sorbent cartridge according to claim 1, wherein the central casing is substantially cylindrical in shape.

18. A sorbent cartridge configured for use in sorbent dialysis, the sorbent cartridge comprising:
a central casing that forms external side walls of the sorbent cartridge, wherein the central casing is capped at both opposing ends, by a bottom cap and a top cap, respectively, such that the central casing, the bottom cap, and the top cap substantially encloses a volume in a watertight manner;
a bottom chamber that occupies a first portion of the volume, wherein the bottom chamber is capped by the bottom cap and by a bottom restrictor; wherein the bottom restrictor is disposed opposite from the bottom cap; wherein side walls of the bottom chamber are formed from a first portion of the central casing;
the bottom restrictor is a first solid plate that comprises a plurality of first holes that pass entirely through the first solid plate;
a region configured to house sorbent media, wherein the region houses the sorbent media, wherein the region occupies a second portion of the volume; wherein the plurality of first holes are in communication with the region and lead into the region; wherein external side walls of the region are formed from a second portion of the central casing;
a top restrictor that is a second solid plate that comprises a plurality of second holes that pass entirely through the second solid plate; wherein the top restrictor is disposed opposite from the bottom restrictor; wherein the region is in communication with the plurality of second holes;
a top chamber that occupies a third portion of the volume, wherein the top chamber is capped by the top cap and by the top restrictor; wherein the top restrictor is disposed opposite from the top cap; wherein side walls of the top chamber are formed from a third portion of the central casing;
wherein the region comprises a plurality of cylindrical concentric members that run in a direction from the bottom restrictor to the top restrictor; wherein the plurality of cylindrical concentric members are disposed between the bottom restrictor and the top restrictor forming a plurality of concentric compartments with a center most compartment that is substantially cylindrical in shape and a plurality of cylindrical concentric annular shaped compartments around the center most compartment;
wherein in use, a dialysate fluid stream enters the sorbent cartridge at the bottom chamber; then is partially obstructed by the bottom restrictor before entering the region; then engages with the sorbent media; then is partially obstructed by the top restrictor before entering the top chamber; and then exits the sorbent cartridge from the top chamber.

19. The sorbent cartridge according to claim 18, wherein the sorbent cartridge comprises a plurality of paired holes, wherein a given pair of holes selected from the plurality of paired holes is a first hole selected from the plurality of first holes and a second hole selected from the plurality of second holes; wherein each hole selected from the given pair of holes is colinearly aligned with the other hole of that given pair of holes.

20. The sorbent cartridge according to claim 19, wherein each hole selected from the given pair of holes has a different diameter from the other hole of that given pair of holes.

21. The sorbent cartridge according to claim 18, wherein the plurality of first holes has first holes located closer to a center of the bottom restrictor and has different first holes located closer to an outer edge of the bottom restrictor; wherein the first holes located closer to the center of the bottom restrictor are smaller in diameter than the different first holes located closer to the outer edge of the bottom restrictor.

22. The sorbent cartridge according to claim 18, wherein the plurality of concentric compartments are elongate and are substantially hollow and configured to house at least some of the sorbent media.

23. The sorbent cartridge according to claim 22, wherein the plurality of concentric compartments are subdivided into upper and lower compartments, wherein the upper and lower compartments are arranged end to end with respect to each other.

24. The sorbent cartridge according to claim 23, wherein each of the upper and lower compartments are configured to house at least a portion of the sorbent media.

25. The sorbent cartridge according to claim 23, wherein the sorbent cartridge comprises at least one layer that is disposed between the upper and lower compartments, wherein the at least one layer is comprised of a semipermeable membrane that is configured to allow passage of the dialysate fluid stream but that blocks migration of the sorbent media.

26. The sorbent cartridge according to claim 18, wherein opposite ends of the plurality of cylindrical concentric members are touching the bottom restrictor and the top restrictor, respectively.

27. The sorbent cartridge according to claim 18, wherein each concentric compartment selected from the plurality of concentric compartments is configured to house at least some of the sorbent media.

28. The sorbent cartridge according to claim 18, wherein the sorbent cartridge comprises at least one interim restrictor; wherein the at least one interim restrictor is disposed between the bottom restrictor and the top restrictor; wherein the at least one interim restrictor is a third solid plate that comprises a plurality of third holes that pass entirely through the third solid plate; wherein the at least one interim restrictor is configured to partially obstruct the dialysate fluid stream.

29. The sorbent cartridge according to claim 18, wherein the central casing is substantially cylindrical in shape.

\* \* \* \* \*